(12) United States Patent
Campbell

(10) Patent No.: US 8,585,687 B2
(45) Date of Patent: Nov. 19, 2013

(54) COMBINED WAVEFRONT AND TOPOGRAPHY SYSTEMS AND METHODS

(75) Inventor: Charles E. Campbell, Berkeley, CA (US)

(73) Assignee: AMO Development, LLC, Santa Ana, CA (US)

(*) Notice: Subject to any disclaimer, the term of this patent is extended or adjusted under 35 U.S.C. 154(b) by 1403 days.

(21) Appl. No.: 12/119,293

(22) Filed: May 12, 2008

(65) Prior Publication Data

US 2008/0281304 A1 Nov. 13, 2008

Related U.S. Application Data

(60) Provisional application No. 60/917,579, filed on May 11, 2007.

(51) Int. Cl.
*A61B 18/20* (2006.01)

(52) U.S. Cl.
USPC .................................. 606/5; 606/4

(58) Field of Classification Search
USPC .......................... 606/4, 5; 128/898
See application file for complete search history.

(56) References Cited

U.S. PATENT DOCUMENTS

| | | |
|---|---|---|
| 4,159,867 A | 7/1979 | Achatz et al. |
| 4,312,574 A | 1/1982 | Wilms |
| 4,420,228 A | 12/1983 | Humphrey |
| 4,440,477 A | 4/1984 | Schachar |
| 4,530,579 A | 7/1985 | Hyde |
| 4,569,576 A | 2/1986 | Karpov et al. |
| 4,588,270 A | 5/1986 | Tamaki |
| 4,662,730 A | 5/1987 | Outwater et al. |
| 4,666,269 A | 5/1987 | Nakamura et al. |
| 4,761,071 A | 8/1988 | Baron |
| 4,902,123 A | 2/1990 | Yoder, Jr. |
| 4,917,458 A | 4/1990 | Matsumura |
| 4,993,826 A | 2/1991 | Yoder, Jr. |
| 4,998,819 A | 3/1991 | Labinger et al. |
| 5,054,907 A | 10/1991 | Sklar et al. |
| 5,062,702 A | 11/1991 | Bille |
| 5,106,183 A | 4/1992 | Yoder, Jr. |
| 5,110,200 A | 5/1992 | Snook |

(Continued)

FOREIGN PATENT DOCUMENTS

| | | |
|---|---|---|
| DE | 19538567 | 4/1997 |
| FR | 2828396 | 2/2003 |

(Continued)

OTHER PUBLICATIONS

Klein, Stanley A., "Optimal Corneal Ablation for Eyes with Arbitrary Hartmann-Shack Aberrations," J. Opt. Soc. Am. A, vol. 15 (Sep. 1998), No. 9, pp. 2580-2588.

(Continued)

*Primary Examiner* — Bill Thomson
*Assistant Examiner* — Jeffrey Lipitz
(74) *Attorney, Agent, or Firm* — AMO Development, LLC

(57) ABSTRACT

Methods, software, and systems are provided for determining an ablation target shape for a treatment for an eye of a patient. Techniques include determining wavefront information from the eye of the patient with a wavefront eye refractometer, determining anterior corneal shape information from the eye with a corneal topography device, and combining the wavefront information and the anterior corneal shape information to determine the ablation target shape.

24 Claims, 10 Drawing Sheets

(56) References Cited

U.S. PATENT DOCUMENTS

| | | |
|---|---|---|
| 5,283,598 A | 2/1994 | McMillan et al. |
| 5,349,398 A | 9/1994 | Koester |
| 5,392,079 A | 2/1995 | Federov et al. |
| 5,418,582 A | 5/1995 | van Saarloos |
| 5,500,697 A | 3/1996 | Fujieda |
| 5,585,873 A | 12/1996 | Shalon et al. |
| 5,640,962 A | 6/1997 | Jean et al. |
| 5,684,562 A | 11/1997 | Fujieda |
| 5,793,468 A | 8/1998 | Shalon et al. |
| 5,847,804 A | 12/1998 | Sarver et al. |
| 5,864,383 A | 1/1999 | Turner et al. |
| 5,867,250 A | 2/1999 | Baron |
| 5,873,832 A | 2/1999 | Maloney et al. |
| 5,886,767 A | 3/1999 | Snook |
| 5,909,270 A | 6/1999 | Moser et al. |
| 5,920,373 A | 7/1999 | Bille |
| 5,929,970 A | 7/1999 | Mihashi |
| 5,953,100 A | 9/1999 | Sarver et al. |
| 5,993,000 A | 11/1999 | Kobayashi et al. |
| 6,007,204 A | 12/1999 | Fahrenkrug et al. |
| 6,042,233 A | 3/2000 | Mihashi et al. |
| 6,048,065 A | 4/2000 | Davis et al. |
| 6,050,687 A | 4/2000 | Bille |
| 6,059,773 A | 5/2000 | Maloney et al. |
| 6,070,981 A | 6/2000 | Mihashi et al. |
| 6,079,831 A | 6/2000 | Sarver et al. |
| 6,086,204 A | 7/2000 | Magnante |
| 6,116,738 A | 9/2000 | Rorabaugh |
| 6,120,150 A | 9/2000 | Sarver et al. |
| 6,129,722 A | 10/2000 | Ruiz |
| 6,152,565 A | 11/2000 | Liu et al. |
| 6,234,631 B1 | 5/2001 | Sarver et al. |
| 6,234,978 B1 | 5/2001 | Mihashi et al. |
| 6,257,723 B1 | 7/2001 | Sarver et al. |
| 6,271,914 B1 | 8/2001 | Frey et al. |
| 6,271,915 B1 | 8/2001 | Frey et al. |
| 6,299,309 B1 | 10/2001 | Ruiz |
| 6,305,802 B1 | 10/2001 | Roffman et al. |
| 6,379,008 B1 | 4/2002 | Chateau et al. |
| 6,382,795 B1 | 5/2002 | Lai |
| 6,394,605 B1 | 5/2002 | Campin et al. |
| 6,428,168 B2 | 8/2002 | Sarver et al. |
| 6,447,119 B1 | 9/2002 | Stewart et al. |
| 6,460,997 B1 | 10/2002 | Frey et al. |
| 6,467,907 B1 | 10/2002 | Fujieda et al. |
| 6,497,483 B2 | 12/2002 | Frey et al. |
| 6,511,179 B1 | 1/2003 | Davis et al. |
| 6,511,180 B2 | 1/2003 | Guirao et al. |
| 6,525,883 B2 | 2/2003 | Hirohara et al. |
| 6,540,692 B2 | 4/2003 | Mihashi et al. |
| 6,547,393 B2 | 4/2003 | Ruiz |
| 6,565,209 B2 | 5/2003 | Campin |
| 6,569,154 B2 | 5/2003 | Campin et al. |
| 6,572,230 B2 | 6/2003 | Levine |
| 6,575,573 B2 | 6/2003 | Lai et al. |
| 6,592,574 B1 | 7/2003 | Shimmick et al. |
| 6,598,973 B2 | 7/2003 | Campin |
| 6,598,975 B2 | 7/2003 | Liang et al. |
| 6,601,956 B1 | 8/2003 | Jean et al. |
| 6,607,273 B2 | 8/2003 | Sarver et al. |
| 6,609,794 B2 | 8/2003 | Levine |
| 6,610,048 B1 | 8/2003 | Holladay et al. |
| 6,616,275 B1 | 9/2003 | Dick et al. |
| 6,629,761 B1 | 10/2003 | Hirohara et al. |
| 6,634,752 B2 | 10/2003 | Curatu |
| 6,637,884 B2 | 10/2003 | Martino |
| 6,666,857 B2 | 12/2003 | Smith |
| 6,685,320 B2 | 2/2004 | Hirohara et al. |
| 6,692,126 B1 | 2/2004 | Xie et al. |
| 6,695,450 B2 | 2/2004 | Hirohara et al. |
| 6,705,729 B2 | 3/2004 | Piers et al. |
| 6,739,721 B2 | 5/2004 | Altmann |
| 6,755,528 B2 | 6/2004 | Isogai |
| 6,808,266 B2 | 10/2004 | Youssefi |
| 6,827,444 B2 | 12/2004 | Williams et al. |
| 6,848,790 B1 | 2/2005 | Dick et al. |
| 6,905,209 B2 | 6/2005 | Mihashi et al. |
| 6,913,358 B2 | 7/2005 | Almeida et al. |
| 6,926,408 B2 | 8/2005 | Sarver |
| RE38,839 E | 10/2005 | Magnante |
| 6,988,801 B2 | 1/2006 | Yoon |
| 7,029,119 B2 | 4/2006 | Youssefi et al. |
| 7,036,934 B1 | 5/2006 | Youssefi et al. |
| 7,044,603 B2 | 5/2006 | Yoon |
| 7,044,944 B2 | 5/2006 | Campin et al. |
| 7,146,983 B1 | 12/2006 | Hohla et al. |
| 7,216,980 B2 | 5/2007 | Mihashi et al. |
| 7,222,962 B2 | 5/2007 | Hirohara et al. |
| 7,226,443 B1 | 6/2007 | Campin et al. |
| 7,237,898 B1 | 7/2007 | Hohla et al. |
| 7,249,851 B2 | 7/2007 | Hirohara et al. |
| RE39,882 E | 10/2007 | Mihashi et al. |
| 7,303,281 B2 | 12/2007 | Wakil et al. |
| 7,309,126 B2 | 12/2007 | Mihashi et al. |
| 2003/0069566 A1* | 4/2003 | Williams et al. .................. 606/5 |
| 2003/0144650 A1 | 7/2003 | Smith |
| 2003/0169403 A1 | 9/2003 | Curatu |
| 2004/0019346 A1* | 1/2004 | Chernyak .......................... 606/5 |
| 2004/0021826 A1 | 2/2004 | Sarver et al. |
| 2004/0054358 A1* | 3/2004 | Cox et al. .......................... 606/5 |
| 2004/0066489 A1 | 4/2004 | Benedikt et al. |
| 2006/0152677 A1 | 7/2006 | Youssefi et al. |
| 2006/0209256 A1 | 9/2006 | Beyerlein et al. |
| 2007/0055222 A1* | 3/2007 | Hohla et al. .................... 606/12 |

FOREIGN PATENT DOCUMENTS

| | | |
|---|---|---|
| JP | 11164816 A | 6/1999 |
| MX | PA01010791 A | 4/2003 |
| WO | WO 01/28410 A | 4/2001 |
| WO | WO 03063695 A1 | 8/2003 |
| WO | WO 03077740 A1 | 9/2003 |
| WO | WO 2004/113958 A | 12/2004 |
| WO | WO 2006/100086 A | 9/2006 |
| WO | WO 2007/012924 A | 2/2007 |

OTHER PUBLICATIONS

PCT International Search Report and Written Opinion mailed Oct. 24, 2008; International Application No. PCT/US2008/063465; 16 pages.

\* cited by examiner

COMBINED WAVEFRONT AND TOPOGRAPHY SYSTEMS AND METHODS

CROSS-REFERENCES TO RELATED APPLICATIONS

This application is a nonprovisional of, and claims the benefit of priority to, U.S. Provisional Patent Application No. 60/917,579 filed May 11, 2007. This application is also related to U.S. patent application Ser. No. 11/769,054 filed Jun. 27, 2007. The complete disclosure of each of these filings is incorporated herein by reference for all purposes.

BACKGROUND OF THE INVENTION

Embodiments of the present invention are related to systems and methods for laser vision correction, and in particular to laser refractive correction using wavefront eye refractor and corneal topographical information.

Often in the field of wavefront guided laser refraction, the ablation target is based on the uncorrected wavefront exiting the eye, as measured with a wavefront eye refractor, by converting the wavefront error to wavefront error in corneal tissue. Such approaches typically do not adequately account for transverse ray movement from the measurement location to the point of refraction, do not account for the obliquity of the refracting surface, and/or do not account for local variations in the anterior corneal surface shape.

In light of the above, it would be desirable to provide improved optical measurement devices, systems, and methods. It would be particularly beneficial if these improved techniques could build on the recent advances that have been made in wavefront measurement techniques, particularly if improvements in efficiency and/or accuracy of the measurements could be provided. The present disclosure provide solutions to at least some of these needs.

BRIEF SUMMARY OF THE INVENTION

Embodiments of the present invention provide systems and methods for generating a laser refractive treatment ablation target using wavefront and corneal topographical data. These techniques can involve finding the ablation target for laser vision correction using both wavefront eye refractor and corneal topography information, such that the ablation target provides the desired refractive state for the eye. It thus provides a customized solution for the eye that is to be treated and does so for the desired final result. Advantageously, these approaches can account for transverse ray movement from the measurement location to the point of refraction, for the obliquity of the refracting surface, and/or for local variations in the anterior corneal surface shape. Embodiments disclosed herein provide straightforward solutions for these effects that can be easily implemented.

In an exemplary approach, the wavefront exiting the uncorrected eye and the anterior corneal shape of the eye are measured. Both the exiting wavefront and the corneal shape can be used to determine the amount of tissue that must be removed at each corneal location to result in the desired refractive state for the eye. Full ray tracing can be used to account for oblique surface effects and transverse wavefront propagation effects so that the final surface will accurately create the desired refractive state. Thus the ablation target, if achieved by subsequent treatment, yields the desired refractive effect.

In one aspect, embodiments of the present invention encompass methods for determining an ablation target shape for a laser vision treatment for an eye of a patient. Methods may include, for example, determining or characterizing a wavefront exiting the eye of the patient with a wavefront eye refractometer, determining or characterizing an anterior corneal shape of the eye with a corneal topography device; and combining the wavefront information and the anterior corneal shape information to determine the ablation target shape.

In another aspect, embodiments of the present invention encompass systems for determining an ablation target shape for a laser vision treatment for an eye of a patient. A system may include, for example, a wavefront input module having a tangible medium embodying machine-readable code that receives a wavefront or wavefront information of an eye as determined by a wavefront eye refractometer. A system may also include a topography input module having a tangible medium embodying machine-readable code that receives an anterior corneal shape or anterior corneal shape information of the eye as determined by a corneal topography device. The system may further include a processing module having a tangible medium embodying machine-readable code that combines the wavefront or wavefront information and the anterior corneal shape or shape information to provide the ablation target shape.

In still a further aspect, embodiments of the present invention encompass systems for determining an ablation target shape for a laser vision treatment of an eye of a patient, such that an exemplary system may include a wavefront eye refractometer, a corneal topography device, and a processor coupled with the wavefront eye refractometer and the corneal topography device. The processor can have a tangible medium embodying machine-readable code that combines a wavefront or wavefront information of the eye of the patient from the wavefront eye refractometer with an anterior corneal shape or shape information of the eye of the patient from the corneal topography device so as to provide the ablation target shape.

In yet another aspect, embodiments of the present invention encompass methods for determining an ablation target shape for a laser vision treatment for an eye of a patient. Methods may include, for example, determining a gradient map or map information exiting the eye of the patient with a wavefront measurement system, determining an anterior corneal shape or shape information of the eye with a corneal topography device, and combining the gradient map or map information and the anterior corneal shape or shape information to determine the ablation target shape. In some cases, the gradient map is not based on a reconstructed wavefront.

In some aspects, embodiments of the present invention encompass methods for determining an ablation target shape for a laser vision treatment for an eye of a patient. Methods may include, for example, determining a wavefront measurement or information of the eye of the patient, determining a K value measurement or information corresponding to an anterior corneal shape of the eye, and determining the ablation target shape based on the wavefront measurement or information and the K value measurement or information.

In one aspect, embodiments of the present invention encompass methods for determining an ablation target shape for a treatment, such as a laser vision treatment, for an eye of a patient. Methods may include inputting a surface shape or a surface shape gradient of a pre-operative anterior corneal surface of the eye, and determining a surface shape or a surface shape gradient of a desired post operative anterior corneal surface of the eye based on a measured wavefront or a measured wavefront gradient of the eye, a desired wavefront or a desired wavefront gradient of the eye, and the surface shape or the surface shape gradient of the pre-operative anterior corneal surface of the eye. Methods may also include determining the ablation target shape based on the surface shape or the surface shape gradient of the pre-operative anterior corneal surface and the surface shape or the surface shape gradient of the desired post operative anterior corneal surface. In some methods, the ablation target shape is determined based on a difference between the surface shape or the surface shape gradient of the pre-operative anterior corneal surface and the surface shape or the surface shape gradient of the desired post operative anterior corneal surface. According to some embodiments, methods may also include determining a pre-operative ablation target gradient based on the surface shape or the surface shape gradient of the pre-operative anterior corneal surface, determining a post-operative ablation target gradient based on the surface shape or the surface shape gradient of the post-operative anterior corneal surface, and determining the ablation target shape based on a reconstruction of the pre-operative ablation target gradient and the post-operative ablation target gradient. Optionally, such reconstruction can involve a Fourier reconstruction. In some cases, such reconstruction can involve a data interpolation procedure. In some embodiments, the surface shape or the surface shape gradient of the pre-operative anterior corneal surface shape is based on a topographic analysis of the eye. In some cases, the surface shape or the surface shape gradient of the pre-operative anterior corneal surface shape is based on a keratometric analysis of the eye. In some cases, the surface shape or the surface shape gradient of a desired post-operative anterior corneal surface of the eye is determined by a ray tracing procedure. Methods may also include removing or ablating an amount of corneal tissue from the eye based on the ablation target shape.

In another aspect, embodiments of the present invention encompass systems for determining an ablation target shape for a laser vision treatment for an eye of a patient. Systems may include, for example, a wavefront input module having a tangible medium embodying machine-readable code that receives a wavefront information of an eye as determined by a wavefront sensor, a topography input module having a tangible medium embodying machine-readable code that receives an anterior corneal shape information of the eye as determined by a corneal topography device, and a processing module having a tangible medium embodying machine readable code that combines the wavefront information and the anterior corneal shape information to provide the ablation target shape. In some cases, the wavefront information includes a wavefront value or a wavefront gradient value. In some cases, the anterior corneal shape information includes an anterior corneal shape value or an anterior corneal shape gradient value. Optionally, the wavefront module further includes a tangible medium embodying machine readable code that receives a desired wavefront value or a wavefront gradient value of the eye, and the tangible medium embodying machine-readable code of the processing module combines the wavefront information, the desired wavefront value or the wavefront gradient value, and the anterior corneal shape information to provide the ablation target shape.

In yet another aspect, embodiments of the present invention include systems for determining an ablation target shape for a treatment, such as a laser vision treatment, of an eye of a patient. Systems may include a wavefront sensor, a corneal topography device, and a processor coupled with the wavefront sensor and the corneal topography device, where the processor includes a tangible medium embodying machine-readable code that combines a wavefront information of the eye of the patient from the wavefront sensor with an anterior corneal shape information of the eye of the patient from the corneal topography device so as to provide the ablation target shape.

In another aspect, embodiments of the present invention include methods for determining an ablation target shape for a laser vision treatment for an eye of a patient. Methods include, for example, determining a desired wavefront or wavefront gradient value for the eye of the patient, determining a measured wavefront or wavefront gradient value of the eye of the patient with a wavefront measurement system, determining an anterior corneal shape or anterior corneal shape gradient value of the eye of the patient with a corneal topography device, and combining the desired wavefront or wavefront gradient value, the measured wavefront or wavefront gradient value, and the anterior corneal shape or anterior corneal shape gradient value to determine the ablation target shape. In some cases, the anterior corneal shape or anterior corneal surface shape gradient value includes a surface shape or surface shape gradient of a preoperative anterior corneal surface of the eye. Optionally, methods may include determining a surface shape or surface shape gradient of a postoperative anterior corneal surface of the eye based on the surface shape or surface shape gradient of a preoperative anterior corneal surface of the eye, the desired wavefront or wavefront gradient value, and the measured wavefront or wavefront gradient value. The ablation target shape can be determine based on a difference between the surface shape or surface shape gradient of the preoperative anterior corneal surface and the surface shape or surface shape gradient of the post-operative anterior corneal surface. Methods may also include removing or ablating an amount of corneal tissue from the eye based on the ablation target shape.

In still a further aspect, embodiments of the present invention include methods for calculating or determining an ablation target shape for a laser vision treatment for an eye of a patient. Methods may include determining a wavefront measurement of the eye of the patient, determining a K value measurement corresponding to an anterior corneal shape of the eye, and determining the ablation target shape based on the wavefront measurement and the K value measurement. Methods may also involve removing an amount of corneal tissue from the eye based on the ablation target shape.

In one aspect, embodiments of the present invention encompass methods of determining an ablation target. Methods may include, for example, selecting an ocular performance of an eye, measuring or calculating a first parameter having at least one of a wavefront from an eye or a slope of a wavefront from the eye, measuring or calculating a second parameter having at least one of a shape a cornea of the eye or a slope of the corneal shape of the eye, determining an input parameter having a direction of propagation out of the eye, where the calculation of the input parameter is based on the first parameter and the second parameter. Methods can also include determining an ablation target based on the selected ocular performance and the input parameter. According to some embodiments, the eye has an optical axis and the ocular performance is an angle of a ray from an object at a specified location from the eye along the optical axis. The object may be a point source disposed on the optical axis an infinite distance from the eye. The first parameter can be determined using a wavefront sensor and the second parameter can be determined from a topography measurement. In some embodiments, the wavefront sensor is a Hartmann-Shack wavefront sensor. In some embodiments, the input parameter is a ray propagating from a retina of the eye. Optionally, the first parameter, the second parameter, and the input parameter may be specified from a predetermined location on the cornea.

For a fuller understanding of the nature and advantages of the present invention, reference should be had to the ensuing detailed description taken in conjunction with the accompanying drawings.

DETAILED DESCRIPTION OF THE INVENTION

Embodiments of the present invention can be readily adapted for use with existing laser systems, wavefront measurement systems, and other optical measurement devices. Although systems, software, and method embodiments of the present invention are described primarily in the context of a laser eye surgery system, it should be understood the present invention may be adapted for use in alternative eye treatment procedures, systems, or modalities, such as spectacle lenses, intraocular lenses, accommodating IOLs, contact lenses, corneal ring implants, collagenous corneal tissue thermal remodeling, corneal inlays, corneal onlays, other corneal implants or grafts, and the like. Relatedly, systems, software, and methods according to embodiments of the present invention are well suited for customizing any of these treatment modalities to a specific patient. Thus, for example, embodiments encompass custom intraocular lenses, custom contact lenses, custom corneal implants, and the like, which can be configured to treat or ameliorate any of a variety of vision conditions in a particular patient based on their unique ocular characteristics or anatomy.

Figure 1:
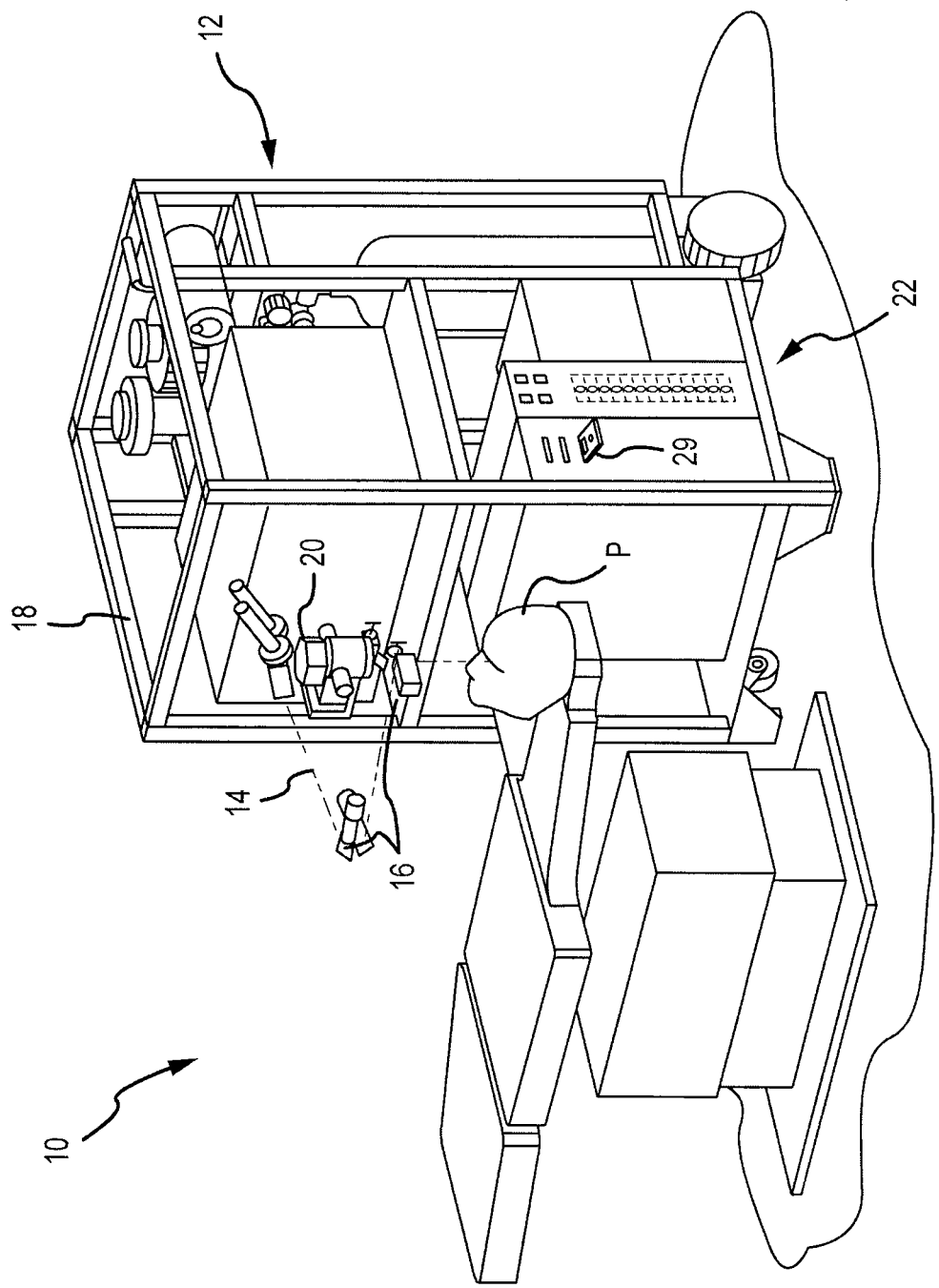
FIG. 1 illustrates a laser ablation system according to an embodiment of the present invention.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with a input device of processor 22, the storage media may also be remotely operatively coupled with processor by means of network connections such as the internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like. Basis data can be further characterized for particular lasers or operating conditions, by taking into account localized environmental variables such as temperature, humidity, airflow, and aspiration.

Figure 2:
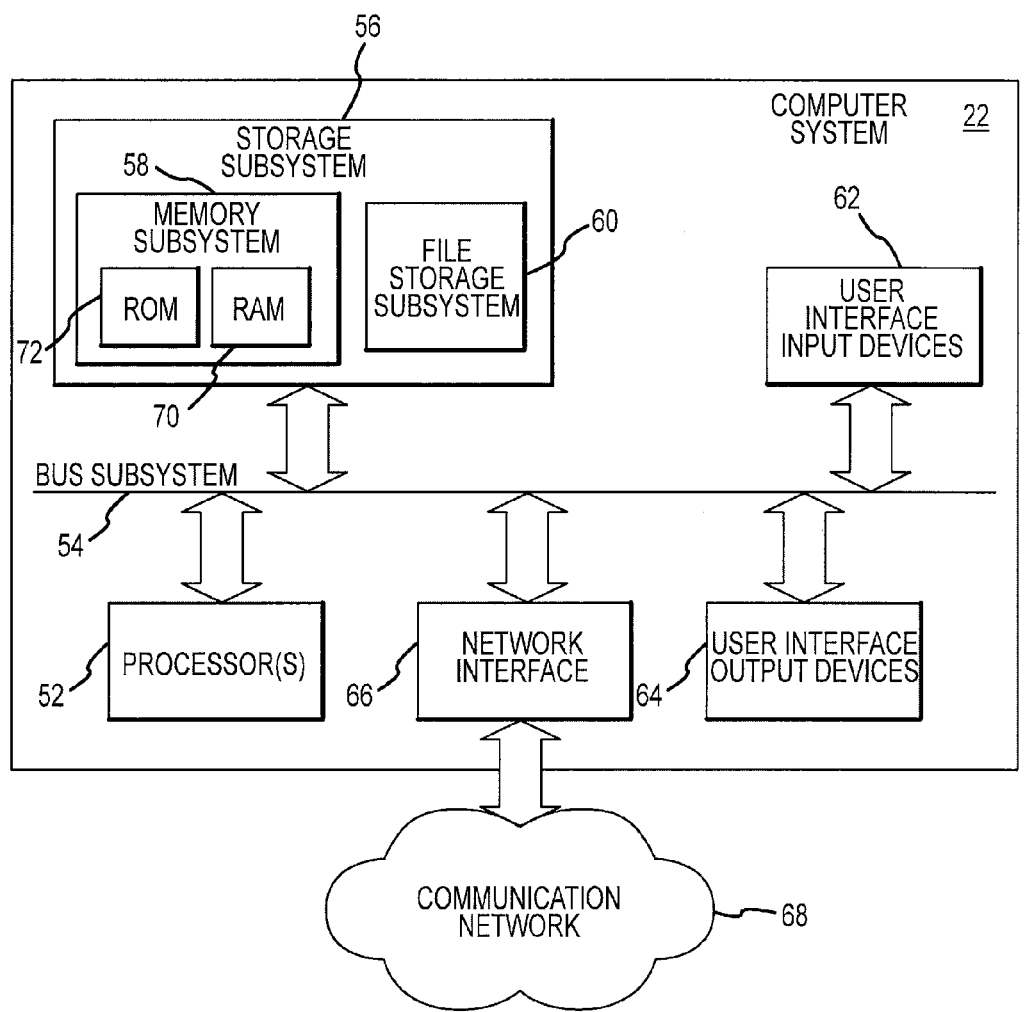
FIG. 2 illustrates a simplified computer system according to an embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
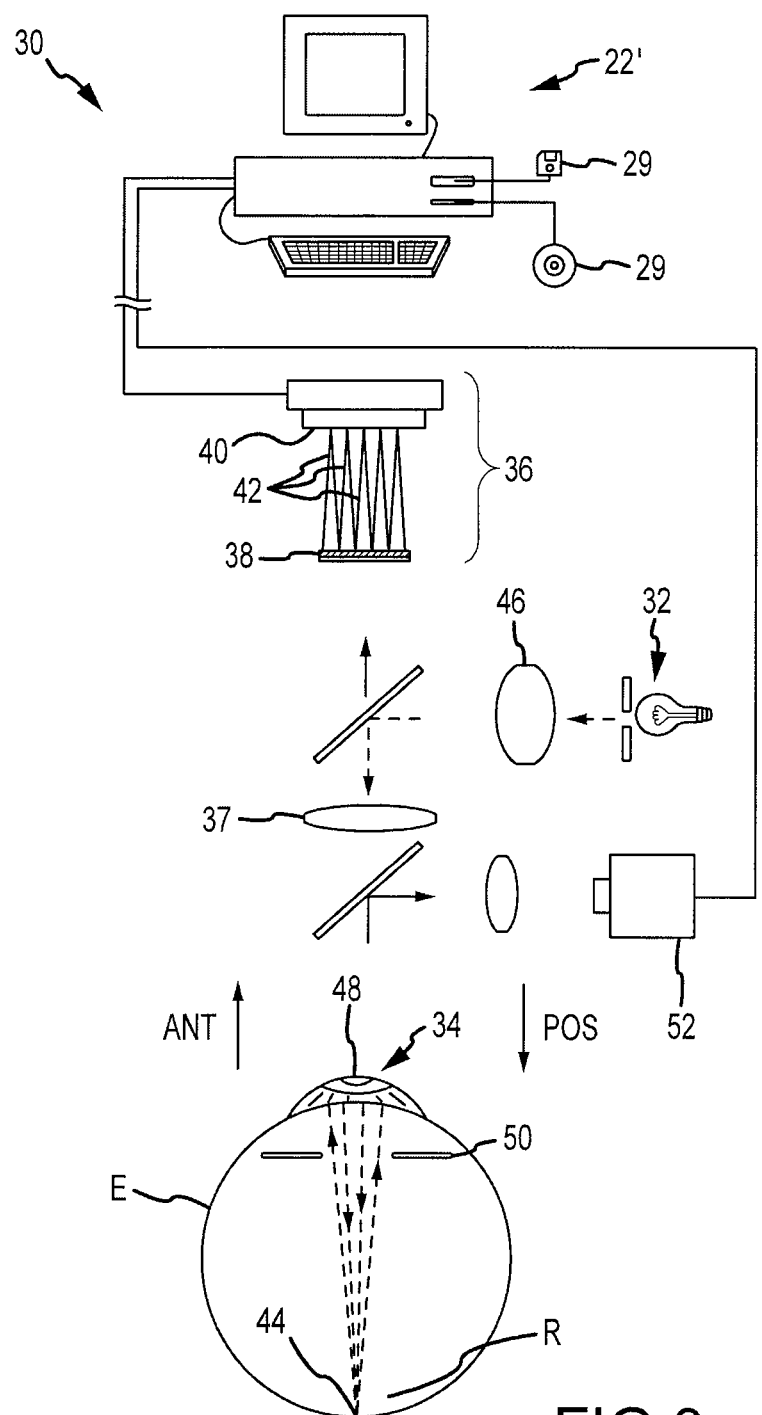
FIG. 3 illustrates a wavefront measurement system according to an embodiment of the present invention.

Referring now to FIG. 3, one embodiment of a wavefront measurement system 30 is schematically illustrated in simplified form. In very general terms, wavefront measurement system 30 is configured to sense local slopes of a wavefront surface map exiting the patient's eye. In the illustrated embodiment, a device based on the Hartmann-Shack principle generally includes a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an illumination or image source 32, such as a laser, which projects a source through optical tissues 34 of eye E so as to form an image or spot 44 upon a surface of retina R. The image 44 from retina R is transmitted by the optical system of the eye (e.g., optical tissues 34) and imaged onto an image sensor 40 of a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and the image sensor 40. As the image 44 from retina R is transmitted through optical tissues 34 and imaged onto a surface of image sensor 40 and an image of the eye pupil P is similarly imaged onto a surface of lenslet array 38, the lenslet array 38 separates the transmitted image of pupil P into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local wavefront gradient of the associated region of optical tissue.

Eye E generally defines an anterior orientation ANT and a posterior orientation POS. Image source 32 generally projects light in a posterior orientation through optical tissues 34 to form image 44 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 and/or system optics 37 may be configured or adapted to decrease any distortion of image 44.

In some embodiments, image source optics 46 may decrease lower order optical errors by compensating for defocus, spherical and/or cylindrical errors of optical tissues 34. Higher order optical errors of the optical tissues may also be compensated through the use of an adaptive optic element, such as a deformable mirror (described below). Use of an image of the source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the devices, systems, and methods of the present invention will generally be described with reference to sensing of a single image 44, a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
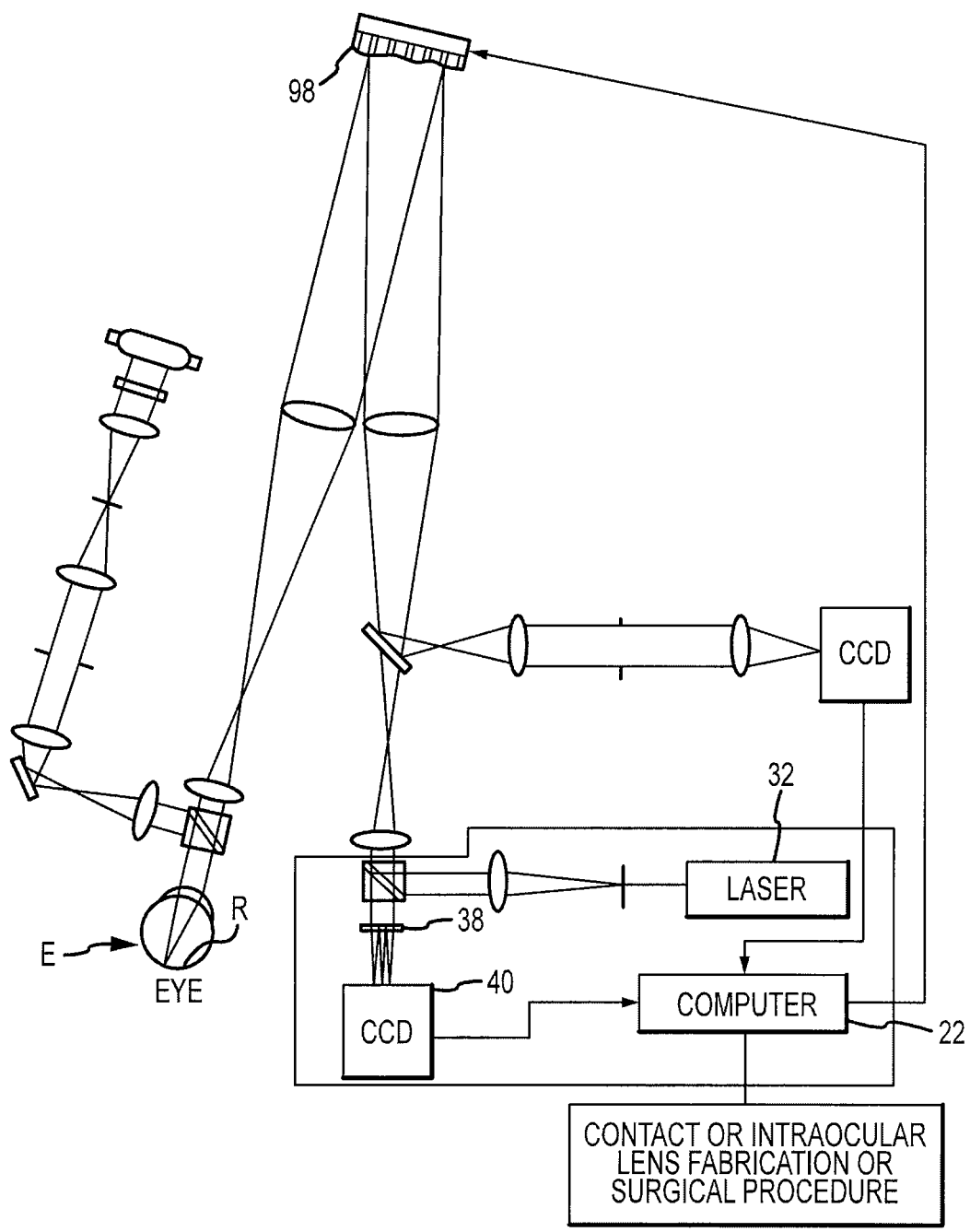
FIG. 3A illustrates another wavefront measurement system according to an embodiment of the present invention.

An alternative embodiment of a wavefront measurement system is illustrated in FIG. 3A. The major components of the system of FIG. 3A are similar to those of FIG. 3. Additionally, FIG. 3A includes an adaptive optical element 53 in the form of a deformable mirror 98. The source image 32 is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations may comprise elements of a WaveScan® system, available from VISX, INCORPORATED of Santa Clara, Calif. One embodiment includes a WaveScan system with a deformable mirror as described above. Alternate embodiments of a wavefront measuring system are described in U.S. Pat. No. 6,271,915 or 6,550,917, the full disclosures of which are incorporated herein by reference. It is appreciated that any wavefront aberrometer could be employed for use with the present invention. Relatedly, embodiments of the present invention encompass the implementation of any of a variety of optical instruments provided by WaveFront Sciences, Inc., including the COAS wavefront aberrometer.

In some embodiments, the wavefront exiting the uncorrected eye is measured with a wavefront eye refractor, which measures the direction of propagation of the rays exiting the image of the Shack-Hartmann lenslet array. The image of this array may be nominally located 3.5 mm posterior to the anterior corneal vertex. The anterior corneal shape can be measured with a corneal topographer. In some instances, for example when a full corneal topography is not available, a standard opthalmometer (keratometer) may be used. The cornea, in the area in which ablation is to take place, is subdivided into a square grid and, using the measure corneal shape information, the corneal surface position and surface gradient values are determined at each grid location. According to some embodiments, any of a variety of refractors, refractometers, aberrometers, and the like may be used to obtain wavefront information. In some embodiments, a Hartmann-Shack aberrometer is used to obtain wavefront or wavefront gradient values. It is understood that in addition to the use of wavefront sensors to obtain information regarding the eye, embodiments encompass the use of other ophthalmic instruments such as Tscherning-style systems, raytrace-type systems, phase diversity sensors, or any other system that can provide a wavefront. Phase diversity sensors are described in, for example, U.S. Pat. Nos. 6,975,457 and 6,439,720, and U.S. Patent Publication No. 2006/0175528. The content of each of these filings is incorporated herein by reference for all purposes.

The measured wavefront gradient information (ray directions) can be used to determine the gradient components of each ray that strikes the corneal surface at a grid location. This can be done by propagating the rays from their measurement plane to the corneal surface while at the same time interpolating within the measure ray gradient fields. The anterior corneal surface normal components, the indices of the refraction on both side of that surface, the un-corrected ray gradient components at each corneal grid location, and the desired ray gradient components (determined from the desired final refraction state) can be used to determine the surface gradient components of the ablation target surface (i.e. the 'tissue lens' that must be removed to produce the desired refractive state). The ablation target surface height information, for example the amount of tissue to be removed at each corneal location, can be calculated from the ablation target gradient information using a method, such as Fourier reconstruction from gradient information or equivalent.

Embodiments of the present invention provide systems and methods for generating a laser refractive treatment ablation target using information on the pre-operative refractive wavefront error and the pre-operative anterior corneal shape. These ablation targets can be used for CustomVue treatments in a VISX Star 4 laser system, and the like. In some embodiments, approaches involve manually entering central corneal curvature values which are used to generate an assumed corneal surface. Some present embodiments encompass the use of full topographic shape information on the anterior corneal surface obtained from a corneal topographer, if it is available. If full topographical data is not available, present embodiments can use other methods of generating a corneal shape. For example, such methods may involve an approach where the wavefront input is the wavefront reconstructed from measured wavefront gradient data measured by a WaveScan system. The gradient of this reconstructed wavefront can be calculated and used to form the rays used in the ray-tracing phase of the method. In some embodiments, there may no need to reconstruct the wavefront from its measured gradients and then re-calculate those gradients. Accordingly, embodiments of the present invention encompass the use of gradients measured by the WaveScan wavefront eye refractor directly.

In some embodiments, systems and methods include expressing the wavefront data and the corneal topography data in the same x,y coordinate system and at the same grid locations, calculating the point of intersection of the measured rays with the measured or assumed anterior corneal surface, calculating the surface normals for the anterior corneal surface to achieve the desired refractive state, and calculating the tissue lens that is removed to create the desired anterior corneal shape or the ablation target. These steps may be performed sequentially.

Expressing the Wavefront Data and the Corneal Topography Data in the Same x,y Coordinate System and at the Same Grid Locations The corneal vertex location, an origin of the coordinate system used by many corneal topography systems, is in general typically displaced from the pupil center, a standard coordinate center for ablation targets. It is helpful to account for this situation. Software can calculate the offset of the corneal vertex from the pupil center. These offset values can be used to correct the x and y positions of the corneal data prior to de-composition into Zernike coefficients. It is also helpful to correct the Shack-Hartmann lenslet center x and y locations to the common coordinate system before calculating the ray intersect locations in the corneal vertex plane.

If the corneal topography data locations are given in a polar coordinate system, i.e. by specifying the meridian angle $\theta$ and radial distance r from the corneal vertex, then before applying the x and y offsets, it may be helpful to convert the polar coordinate to Cartesian coordinates using the equations $$x = r \cos \theta \quad (1)$$

$$y = r \sin \theta \quad (2)$$

It may be helpful for the software to recognize those corneal topography data sets that come from corneal topographers that give location values in polar form so that it will recognize those data sets where the transforms given by Eqs. (1) and (2) are performed prior to applying the offset values.

If the corneal topography system is able to measure both components of the anterior corneal surface gradient, then these values may be used directly in the analysis that follows without calculating the surface gradient values from surface height values. However surface height values may be used to find ray intersect locations.

In some embodiments, corneal topography information and wavefront information are located on a square grid. Corneal topography is often initially given in a polar coordinate system, and is typically interpolated. Thus, it may be helpful to interpolate onto the same location grid that is used for the wavefront gradient data. For interpolation of data on a non-uniform grid onto a square grid, Zernike polynomial decomposition and reconstruction onto the square grid can be used. This approach can work well for corneal topography data and can be used as described herein. In some embodiments, the surface height and location information, with the location information transformed as indicated above so that it is in the common coordinate system, is decomposed into a set of Zernike coefficients given in standard form. This decomposition is done to $8^{th}$ radial order using a diameter that exceeds the pupil size of the individual. This diameter can be standardized at 8 millimeters. The coefficients thus obtained can be used to reconstruct the corneal surface at the desired square grid locations, these location being the same as are used for the wavefront gradient field data. In some embodiments, ablation targets are specified on 101×101, 0.1 mm square grids. The Zernike coefficients thus obtained can also be used to efficiently calculate the corneal surface gradient values at each grid location. This method of calculating the surface gradient values using the Zernike coefficient set is given in Appendix A.

In some embodiments, for example where measured corneal topography data may not be available, it is possible to input measured central corneal curvature values (K values), which can be used to generate corneal surface sagittal values and surface gradient values at all grid locations. A general centered untilted quadric surface can be used for this purpose.

A centered general quadric surface can be completely defined by two central curvature values, Kmax and Kmin, the axis orientation of one of the apical principal meridians, A, and a conic constant associated with a chosen apical meridian, k. For an assumed corneal surface it may be sufficient to chose as the conic constant of the flatter of the two principal meridians the value −0.25. This is a reasonable value for the mean conic constant found in the normal human cornea distribution. The axis value typically given for the central corneal curvature values is that for the flatter of the two meridians.

The wavefront gradient data measured by the WaveScan can be on a 0.4 mm square grid and so it can be interpolated so that data is on the desired 101×101, 0.1 mm grid. This interpolation can be done with wavefront data once the wavefront has been reconstructed from the gradient data, and can be done with a bicubic method. The wavefront reconstruction step may be optional, and may not be performed. The interpolation can be done on the gradient fields themselves. The method given in the following section using a curvature matrix may be used for interpolation. This method is a form of biquadratic interpolation.

Calculation of the Point of Intersection of the Measured Rays with the Measured (or Assumed) Anterior Corneal Surface The Shack-Hartmann sensor and subsequent image processing can determine the gradient components of the central ray of that portion of the measured wavefront passing through each lenslet. In this treatment the surface normals of the wavefront surface can be the measured rays. In some embodiments, the image of the lenslet array lies in a plane perpendicular to the optical axis of the wavefront refractor but this plane is not in the plane of the corneal vertex. Thus the measured rays will generally experience transverse motion as they pass from the plane in which they are measured to the corneal surface. The position of a ray as it passes through the lenslet plane can be known from the geometry of the lenslet array but its position upon intersecting the corneal surface can change due to its transverse motion to positions given by:

$$xp(i,j) = xl(i,j) + v \cdot gradx(i,j) \quad (3)$$

$$yp(i,j) = yl(i,j) + v \cdot grady(i,j) \quad (4)$$

where
xv is the x location of ray (i,j) after propagating distance v;
yv is the y location of ray (i,j) after propagating distance v;
xl is the x location of the center of lenslet (i,j);
yl is the y location of the center of lenslet (i,j);
v is the distance between the image of lenslet array and the intersection point;
gradx is the x gradient component of ray (i,j)—in some embodiments, Alternate_Reconstructor, this is the variable X_Slopes (i,j); and
grady is the y gradient component of ray (i,j)—in some embodiments, Alternate_Reconstructor, this is the variable Y_Slopes (i,j).

In some embodiments, it may be assumed that v=(3.5 mm−sc), which equals the nominal distance from the image of the Shack-Hartmann lenslet array to the corneal vertex of 3.5 mm minus the sagittal height of the anterior corneal surface at the point of intersection.

The anterior corneal surface data can include sagittal height values given at designated locations. In general there may not be a measured ray that intersects the corneal surface at one of these designated locations, and some method of interpolation can be useful to find the gradient values for the ray that does strike a designated corneal location. One useful approach to this problem encompasses using an interpolation method involving the measured ray gradients and the known distance between the lenslet array and the corneal surface at the desired point of intersect. This method is described below.

Figure 4:
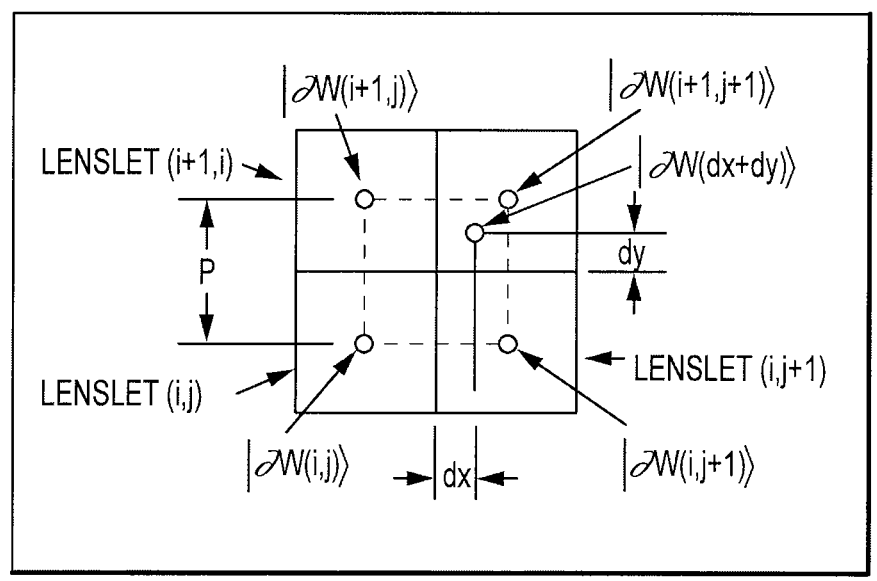
FIG. 4 depicts geometrical aspects of a wavefront according to embodiments of the present invention.

In some embodiments, it may be assumed that the portion of wavefront surface that passes through a square whose corners are the locations of four neighboring measured points can be well approximated by a toric surface and that this toric surface may be specified by a curvature matrix [K] and a mean gradient |∂Wavg⟩, found using the measured gradient values at the four corners. The geometry involved is illustrated in FIG. 4. The measured points are located a distance p apart. The interpolated gradient values, $$|\partial W(dx, dy)\rangle = \begin{pmatrix} \frac{\partial W(dx, dy)}{\partial x} \\ \frac{\partial W(dx, dy)}{\partial y} \end{pmatrix} \quad (5A)$$

are given by the matrix equation $$|\partial W(dx, dy)\rangle = [K]|dr\rangle + |\partial Wavg\rangle \text{ where} \quad (5B)$$

$$|dr\rangle = \begin{pmatrix} dx \\ dy \end{pmatrix} \quad (5C)$$

with dx and dy measured from the midpoint of the four measured locations as shown $$[K] = \begin{bmatrix} Km + Kp & Kx \\ Kx & Km = Kp \end{bmatrix} \quad (5D)$$

where
Km is the mean curvature;
Kp is the curvature of a 'cross cylinder like' element oriented with its principal curvature meridians parallel to the x and y axes; and
Kx is the curvature of a 'cross cylinder like' element oriented with its principal curvature meridians oblique to the x and y axes.

$$|\partial Wavg\rangle = \begin{pmatrix} \frac{\partial Wavg}{\partial x} \\ \frac{\partial Wavg}{\partial y} \end{pmatrix} = \begin{pmatrix} \frac{\left(\frac{\partial W(i,j)}{\partial x} + \frac{\partial W(i+1,j)}{\partial x} + \frac{\partial W(i,j+1)}{\partial x} + \frac{\partial W(i+1,j+1)}{\partial x}\right)}{4} \\ \frac{\left(\frac{\partial W(i,j)}{\partial y} + \frac{\partial W(i+1,j)}{\partial y} + \frac{\partial W(i,j+1)}{\partial y} + \frac{\partial W(i+1,j+1)}{\partial y}\right)}{4} \end{pmatrix} \quad (5E)$$

The values of Km, Kp and Kx within the square defined by four neighboring measured points can be determined using the equations $$Km = \frac{\left\{\begin{array}{c} \frac{\partial W(i,j)}{\partial x} + \frac{\partial W(i+1,j)}{\partial x} - \frac{\partial W(i+1,j+1)}{\partial x} - \frac{\partial W(i,j+1)}{\partial x} \\ \frac{\partial W(i,j)}{\partial y} - \frac{\partial W(i+1,j)}{\partial y} - \frac{\partial W(i+1,j+1)}{\partial y} + \frac{\partial W(i,j+1)}{\partial y} \end{array}\right\}}{4p} \quad (6)$$

$$Kp = \frac{\left\{\begin{array}{c} -\frac{\partial W(i,j)}{\partial x} - \frac{\partial W(i+1,j)}{\partial x} + \frac{\partial W(i+1,j+1)}{\partial x} + \frac{\partial W(i,j+1)}{\partial x} \\ \frac{\partial W(i,j)}{\partial y} - \frac{\partial W(i+1,j)}{\partial y} - \frac{\partial W(i+1,j+1)}{\partial y} + \frac{\partial W(i,j+1)}{\partial y} \end{array}\right\}}{4p} \quad (7)$$

$$Kx = \frac{\left\{\begin{array}{c} -\frac{\partial W(i,j)}{\partial x} + \frac{\partial W(i+1,j)}{\partial x} + \frac{\partial W(i+1,j+1)}{\partial x} - \frac{\partial W(i,j+1)}{\partial x} \\ -\frac{\partial W(i,j)}{\partial y} - \frac{\partial W(i+1,j)}{\partial y} + \frac{\partial W(i+1,j+1)}{\partial y} + \frac{\partial W(i,j+1)}{\partial y} \end{array}\right\}}{4p} \quad (8)$$

The derivation of these equations can be found in C. E. Campbell, "Ray vector fields" J. Opt. Soc. Am. A, 11, 618-622, (1994). The equations can take this form because the points themselves are located at the corners of a square.

Eqs. (3) and (4) can be written as the vector equation $$|rc\rangle = |ra\rangle + v|\partial W(dx, dy)\rangle \quad (9A)$$

where $$|rc\rangle = \begin{pmatrix} xc \\ yc \end{pmatrix} = p\begin{pmatrix} n \\ m \end{pmatrix} \quad (9B)$$

xc is the x value of the specified corneal surface location;
ye is the y value of the specified corneal surface location;
n is the number of x grid intervals between the origin of the grid where x=y=0 and the specified corneal location;
m is the number of y grid intervals between the origin of the grid where x=y=0 and the specified corneal location;

$$|ra\rangle = \begin{pmatrix} xa \\ ya \end{pmatrix} = \begin{pmatrix} x(i,j) + p/2 + dx \\ y(i,j) + p/2 + dy \end{pmatrix} = p\begin{pmatrix} j+1/2 \\ i+1/2 \end{pmatrix} + |dr\rangle \quad (9C)$$

xa=x(i,j)+p/2+dx is the x value of the location in the lenslet array from which the intersect ray originates;
ya=y(i,j)+p/2+dy is the y value of the location in the lenslet array from which the intersect ray originates; and $$|\partial W(dx, dy)\rangle = \begin{pmatrix} \frac{\partial W(dx, dy)}{\partial x} \\ \frac{\partial W(dx, dy)}{\partial y} \end{pmatrix}$$

is the gradient vector of the intersect ray.
The indices i and y can be defined as $$i = m + k \quad (9D)$$

$$j = n + h \quad (9E)$$

where
  h is the signed number of x grid intervals between the corneal location and the lower, left point of the square from which the ray originates; and
  k is the signed number of y grid intervals between the corneal location and the lower, left point of the square from which the ray originates.

The equation for |ra⟩ can be written as $$|ra\rangle = p\begin{pmatrix} j+1/2 \\ i+1/2 \end{pmatrix} = |dr\rangle = p\begin{pmatrix} n \\ m \end{pmatrix} + p\begin{pmatrix} h+1/2 \\ k+1/2 \end{pmatrix} + |dr\rangle \quad (9F)$$

These definitions allow Eq. (9A) to be rearranged to read $$|rc\rangle - v|\partial W(dx, dy)\rangle - p\begin{pmatrix} n \\ m \end{pmatrix} - p\begin{pmatrix} h+1/2 \\ k+1/2 \end{pmatrix} = |dr\rangle \quad (9G)$$

This expression can be substituted in Eq. (5) to give $$|\partial W(dx, dy)\rangle = [K] \left\{ |rc\rangle - v|\partial W(dx, dy)\rangle - p\binom{n}{m} - p\binom{h+1/2}{k+1/2} \right\} + |\partial Wavg\rangle \quad (9H)$$

$$|\partial W(dx, dy)\rangle = [K] \left\{ p\binom{n}{m} - v|\partial W(dx, dy)\rangle - p\binom{n}{m} - p\binom{h+1/2}{k+1/2} \right\} + |\partial Wavg\rangle \quad (9I)$$

$$|\partial W(dx, dy)\rangle = [K] \left\{ -v|\partial W(dx, dy)\rangle - p\binom{h+1/2}{k+1/2} \right\} + |\partial Wavg\rangle \quad (9J)$$

Now solving for $|\partial W(dx, dy)\rangle$ gives $$\{[I + v[K]]\}|\partial W(dx, dy)\rangle = [K] \left\{ -p\binom{h+1/2}{k+1/2} \right\} + |\partial Wavg\rangle \quad (9K)$$

$$|\partial W(dx, dy)\rangle = \{[I + v[K]]\}^{-1} \left\{ [K] \left\{ -p\binom{h+1/2}{k+1/2} \right\} + |\partial Wavg\rangle \right\} \quad (9L)$$

$$|\partial W(dx, dy)\rangle = \{[I + v[K]]\}^{-1} |\partial Wavg\rangle - p\{[I + v[K]]\}^{-1} [K] \binom{h+1/2}{k+1/2} \quad (10A)$$

Since $$\{[I + v[K]]\} = \begin{bmatrix} 1 + v(Km + Kp) & vKx \\ vKx & 1 + v(Km - Kp) \end{bmatrix} \quad (10B)$$

$$\{[I + v[K]]\}^{-1} = \frac{\begin{bmatrix} 1 + v(Km - Kp) & -vKx \\ -vKx & 1 + v(Km + Kp) \end{bmatrix}}{1 + 2vKm + v^2(Km^2 - Kp^2 - Kx^2)} \quad (10C)$$

and $$\{[I + v[K]]\}^{-1}[K] = \frac{\begin{bmatrix} Km + Kp + v(Km^2 - Kp^2 - Kx^2) & Kx \\ Kx & Km - Kp + v(Km^2 - Kp^2 - Kx^2) \end{bmatrix}}{1 + 2vKm + v^2(Km^2 - Kp^2 - Kx^2)} \quad (10D)$$

$$\{[I + v[K]]\}^{-1}[K] = \frac{[K] + v(Km^2 - Kp^2 - Kx^2)[I]}{1 + 2vKm + v^2(Km^2 - Kp^2 - Kx^2)} \quad (10E)$$

A preliminary step in determining the intersection ray gradients can include determining the square in which this ray is located. The process can include assuming that the gradient values for the intersection ray are not too different from the values determined at the same location in the array as the specified corneal location, and taking these gradient values as those of the lower, left location of the interpolation square. The equations $$h = \text{floor}\left(-\frac{v\frac{\partial W(m,n)}{\partial x}}{p}\right) \quad (10F)$$

$$k = \text{floor}\left(-\frac{v\frac{\partial W(m,n)}{\partial y}}{p}\right)$$

can give the number of grid intervals there are between the corneal location and the lower, left corner of the interpolation square. The values for h and k in turn can allow the values of Km, Kp and Kx to be calculated and using these curvatures values, the values of the gradient components of the intersect ray are found using Eq. (10A).

Embodiments encompass techniques that involve determining the gradients of the intersecting rays. In some cases, embodiments address cases where corneal surface locations are on the boundaries of the ablation area. It may be helpful in implementing the interpolation techniques to provide gradient values at all 4 corners of a square interpolation area. When a surface location is at the edge of the ablation area, the gradient value square from which the intercept ray originates is often outside the ablation area. In these cases there are times when there are not gradient values existing at all 4 corners of that square. It may be difficult to use this square for interpolation. In some cases it is helpful to so identify this square so that an alternative plan can be used. To identify gradient value squares that are valid, in the sense that there are values at all 4 corners, a preliminary step in the ray intercept procedure involves checking each square, indexed by its lower left corner, and placing, for example, a 1 at that location in a 100×100 validity array if the square is 'valid' and a 0 at the location if it is not. Embodiments encompass similar validity designation techniques.

A ray intercept process can be performed for surface location (m,n). Index values h and k can be calculated for surface location (m,n) so that in the interpolation square index values i and j are established. These index value can be checked to determine if the square is 'valid'. If the square is valid, the interpolation process can proceed with square (i,j). If the square is not valid, the other square neighboring surface location (m,n) can be examined until a valid square is found. It can be assumed that the curvature values determined for this valid square are quite similar to those that would have been determined in the non-valid square originally found and can be used for interpolation. The curvature values can be determined for this neighboring valid square and the procedure can proceed as before. This procedure is algorithmically efficient. Similarly, it may be only applied to a few locations and thus may have little or no adverse effect on the final results.

Calculation of the Surface Normals for the Anterior Corneal Surface to Achieve the Desired Refractive State The ray direction just prior to refraction at the anterior corneal surface can be determined by ray tracing the measured ray back through that surface using standard vector ray tracing equations. To make these calculations the three components of the unit vector representing the ray direction, the three components of the unit vector of the surface normal at the point of ray intersection and indices of refraction of the media on both sides of the refracting surface can be used. The unit vector representing the measured ray $|R\rangle$ can include components $$|R\rangle = \begin{pmatrix} Rx \\ Ry \\ Rz \end{pmatrix} = \begin{pmatrix} \dfrac{-\partial W/\partial x}{\sqrt{1+(\partial W/\partial x)^2+(\partial W/\partial y)^2}} \\ \dfrac{-\partial W/\partial y}{\sqrt{1+(\partial W/\partial x)^2+(\partial W/\partial y)^2}} \\ \dfrac{1}{\sqrt{1+(\partial W/\partial x)^2+(\partial W/\partial y)^2}} \end{pmatrix} \quad (10G)$$

The partial derivatives of the wavefront are described in the preceding section. The unit vector representing the corneal surface normal $|N\rangle$ can include components $$|N\rangle = \begin{pmatrix} Nx \\ Ny \\ Nz \end{pmatrix} = \begin{pmatrix} \dfrac{-\partial C/\partial x}{\sqrt{1+\partial C/\partial x^2+\partial C/\partial y^2}} \\ \dfrac{-\partial C/\partial y}{\sqrt{1+\partial C/\partial x^2+\partial C/\partial y^2}} \\ \dfrac{1}{\sqrt{1+\partial C/\partial x^2+\partial C/\partial y^2}} \end{pmatrix} \quad (10H)$$

The constant of proportionality used in the vector refraction equation, $\Gamma$, can be given by the equation $$\Gamma = n_{in}\langle R|N\rangle - \sqrt{n_{in}^2(\langle R|N\rangle^2 - 1) + n_{out}^2} \quad (10I)$$

where $$\langle R|N\rangle = Rx \cdot Nx + Ry \cdot Ny + Rz \cdot Nz; \quad (10J)$$

$n_{in} = 1.000$, the index of refraction of air; and (10K)

$n_{out} = 1.376$, the index of refraction of the corneal stroma. (10L)

In some embodiments further calculation associated with ray tracing may not be performed, because the values determined to this point may be sufficient to determine the desired anterior corneal surface, once the desired ray direction following correction has been designated. This conclusion can be supported as follows.

To make the demonstration, it is helpful to consider the vector refraction equation, which can be written as:

$$n_{out}|Rr\rangle = n_{in}|R\rangle - \Gamma|N\rangle \quad (10M)$$

where $|R\rangle$ is a unit vector representing the ray before refraction; and $|Rr\rangle$ is a unit vector representing the ray after refraction.

$|R_{corr}\rangle$ can represent the rays just before they are refracted by the anterior corneal surface. In some embodiments this vector field can be the same before and after treatment because it can be assumed that only that anterior surface of corneal changes and the other optical surfaces and elements in the eye are unchanged. Therefore if the exiting rays following treatment are designated $|Rt\rangle$, the normals to the corneal surface after treatment can be designated $|Nt\rangle$ and the constant of proportionality after treatment $\Gamma_t$, the vector equation becomes $$n_{out}|R_{corr}\rangle = n_{in}|Rt\rangle - \Gamma_t|Nt\rangle \quad (10N)$$

whereas before treatment the vector equation is $$n_{out}|R_{corr}\rangle = n_{in}|R\rangle - \Gamma|N\rangle \quad (10O)$$

Because there may be no change in $|R_{corr}\rangle$ following treatment, the right sides of both vector equations may be set equal. Using $n_{in}=1.000$, $$|R\rangle - \Gamma|N\rangle = |Rt\rangle - \Gamma_t|Nt\rangle \quad (10P)$$

$$|Rt\rangle - |R\rangle + \Gamma|N\rangle = \Gamma_t|Nt\rangle \quad (10Q)$$

Because the equality of the above equation may also be true for each of the components of the vectors, it may also be true that $$Rtx - Rx + \Gamma Nx = \Gamma_t Ntx \quad (10R)$$

$$Rty - Ry + \Gamma Ny = \Gamma_t Nty \quad (10S)$$

$$Rtz - Rz + \Gamma Nz = \Gamma_t Ntz \quad (10T)$$

The following two ratios can be formed from these three component equations.

$$\frac{Rtx - Rx + \Gamma Nx}{Rtz - Rz + \Gamma Nz} = \frac{\Gamma_t Ntx}{\Gamma_t Ntz} = \frac{Ntx}{Ntz} = \frac{-\partial Ct}{\partial x} \quad (11)$$

$$\frac{Rty - Ry + \Gamma Ny}{Rtz - Rz + \Gamma Nz} = \frac{\Gamma_t Nty}{\Gamma_t Ntz} = \frac{Nty}{Ntz} = \frac{-\partial Ct}{\partial y} \quad (12)$$

On the left hand side of the above ratio equations all values are measured, known, or can be calculated from measured values. On the right hand side of the above ratio equations are the gradient components of the desired anterior corneal surface. These are the values that can be used to determine the ablation target and so they may be determined without calculating the refracted rays.

In some embodiments it is helpful to provide information on the desired refractive error following treatment, i.e. $|Rt\rangle$. A common desired result of a refractive correction is to leave no residual aberration for the case of distant vision. Thus the desired wavefront exiting the eye following treatment can be one where all or substantially all rays are parallel to one another. In such a wavefront, all or most of the rays can be characterized by the same unit vector that has the simple structure $$|Rt\rangle = \begin{pmatrix} 0 \\ 0 \\ 1 \end{pmatrix} \quad (13A)$$

In some cases, it may be desirable to have a refraction other emmetropia, or other than 0 diopters residual refractive error. In some embodiments, it is possible to insert or determine a desired refraction that is different from a desired residual refractive error result, because a wavefront measurement may be done at an infrared wavelength and the correction may be referenced to visible light. This wavelength offset may be desired for automatic refractors or wavefront refractors. In some embodiments, a refractive offset is about 0.5 D and may be refractive error insensitive. In some cases, such approaches may involve a correction or adjustment by offsetting the value of S, where S represents a desired residual spherical error of the eye given in units of diopters.

In some embodiments, another common desired result is a simple spherical refractive error. This may be chosen from a number of reasons, one being the case of a monovision correction for presbyopia where one eye becomes emmetropic and the other eye is left with enough myopia to enable the person to read easily at typical reading distances. If the desired residual spherical error of the eye given in units of diopters as S, then all or substantially all rays exiting the eye will come to a focus at a distance −1/S from the corneal vertex. The negative sign can be used because distances in front of the eye are assigned positive values. Thus the distance from the corneal surface to the focal plane for ray (i,j), d(i,j), can be equal to $$d(i, j) = z(i, j) - \frac{1000}{S} \tag{13B}$$

when S is given in diopters and d is given in millimeters. z is the distance from the corneal vertex plane to the corneal surface at the intersection point for ray (i,j) which can be determined using the method given above for calculating the surface normals. The gradient components for ray(i,j) can be determined, using the above value for d and the values for the x and y ray intersect locations, as $$gradx(i, j) = \frac{-x(i, j)}{d(i, j)} = \frac{x(i, j)}{\frac{1000}{S} - z(i, j)} = \frac{x(i, j)S}{1000 - z(i, j)S} \tag{14}$$

$$grady(i, j) = \frac{-y(i, j)}{d(i, j)} = \frac{y(i, j)}{\frac{1000}{S} - z(i, j)} = \frac{y(i, j)S}{1000 - z(i, j)S} \tag{15A}$$

The components of the unit vector for this ray can be given by $$|Rt(i, j)\rangle = \begin{pmatrix} \frac{gradx(i, j)}{\sqrt{1 + gradx(i, j)^2 + grady(i, j)^2}} \\ \frac{grady(i, j)}{\sqrt{1 + gradx(i, j)^2 + grady(i, j)^2}} \\ \frac{1}{\sqrt{1 + gradx(i, j)^2 + grady(i, j)^2}} \end{pmatrix} \tag{16A}$$

$$|Rt(i, j)\rangle = \begin{pmatrix} \frac{x(i, j)S}{\sqrt{(1000 - z(i, j)S)^2 + x(i, j)^2 + y(i, j)^2}} \\ \frac{y(i, j)S}{\sqrt{(1000 - z(i, j)S)^2 + x(i, j)^2 + y(i, j)^2}} \\ \frac{1000 - z(i, j)S}{\sqrt{(1000 - z(i, j)S)^2 + x(i, j)^2 + y(i, j)^2}} \end{pmatrix} \tag{16B}$$

If a more complex residual wavefront error is desired, for instance if a multifocal presbyopia treatment is desired, then the desired wavefront can be specified as an analytic formula so that the partial derivatives of this wavefront may be found at each ray intersection location. If the desired wavefront is designated W(x(i,j),y(i,j)), the unit vector giving the desired ray(i,j) can be given by $$|Rt(i, j)\rangle = \begin{pmatrix} \frac{-\partial W(x(i, j), y(i, j))/\partial x}{\sqrt{1 + \partial W(x(i, j), y(i, j))/\partial x^2 + \partial W(x(i, j))/\partial y^2}} \\ \frac{-\partial W(x(i, j), y(i, j))/\partial y}{\sqrt{1 + \partial W(x(i, j), y(i, j))/\partial x^2 + \partial W(x(i, j), y(i, j))/\partial y^2}} \\ \frac{1}{\sqrt{1 + \partial W(x(i, j), y(i, j))/\partial x^2 + \partial W(x(i, j), y(i, j))/\partial y^2}} \end{pmatrix} \tag{17}$$

Calculation of the Tissue Lens that is Removed to Create the Desired Anterior Corneal Shape In some embodiments, the gradient components of the anterior corneal shape that are used to supply the desired refractive state can be determined using Eqs. (11) and (12). The shape can be theoretically specified based on these equations. In some cases, embodiments may not involve reconstructing the shape to determine the ablation target, or the tissue lens that is removed to produce the desired anterior corneal shape. In some embodiments, the reconstruction may not be performed for the following reason.

The ablation target At(x,y) can be, by definition, the difference between the pre-treatment anterior corneal surface, C(x,y) and the post-treatment anterior corneal surface Ct(x, y). So the expression for the ablation target can be written as $$At(x, y) = C(x, y) - Ct(x, y) \tag{18'}$$

therefore $$\frac{\partial At(x, y)}{\partial x} = \frac{\partial C(x, y)}{\partial x} - \frac{\partial Ct(x, y)}{\partial x} \tag{18}$$

$$\frac{\partial At(x, y)}{\partial y} = \frac{\partial C(x, y)}{\partial y} - \frac{\partial Ct(x, y)}{\partial y} \tag{19}$$

The quantities on the right hand side of Eqs. (18) and (19) may have already been calculated as described above. Thus, the gradients of the ablation target may have been determined and may be used directly to find the ablation target surface values.

There are a number of ways to generate a surface from known surface gradients, one of which is a method of numerical integration. Another method is a Fourier transform method to reconstruct wavefronts from their measured gradients. The Fourier transform method involves gradient values that are located on a square location grid. The solution for the ablation gradient values can be constructed so that these values do lie on a square grid for this specified reason.

As is done in the case of some wavefront reconstruction method embodiments, the desired ablation target shape, At, can be reconstructed from its gradient fields using the following equations and Eqs. (18) and (19), where $\Im(f)$ indicates the Fourier transform of function $f$.

$$\Im\{At\} = \frac{-i\left(u\Im\left\{\frac{\partial At}{\partial x}\right\} + v\Im\left\{\frac{\partial At}{\partial y}\right\}\right)}{u^2 + v^2} \tag{20}$$

For a rectangular array of gradient data of size N×M given on a square grid with pitch width pw, such that index values i run from 1 to N and index value j run from 1 to M, values of u(i,j) and v(i,j) can be given by $$u(i, j) = \frac{2\pi}{N \cdot pw}\left(i - \frac{N}{2} - 1\right) \quad (21)$$

$$v(i, j) = \frac{2\pi}{M \cdot pw}\left(j - \frac{M}{2} - 1\right) \quad (22)$$

A Fourier transform of the desired ablation target surface can be determined using Eq. (20). The surface itself can be determined by performing an inverse Fourier transform and then calculating the modulus of the values determined.

Some embodiments do not include accounting for the index of refraction of the stromal tissue at this point. This is because the index of refraction effect can be fully taken into account when the gradients of the desired anterior surface are determined.

In some embodiments when the Fourier method is not used, data interpolation can be used because the WaveScan data has the density of the Shack-Hartmann lenslet array used, which has a 0.4 mm pitch, whereas treatment plans are created from data on a square grid with a 0.1 mm pitch. From the point of view of the computer execution time involved, it may be desirable to use a 0.4 mm grid, the natural WaveScan grid size, reconstruct the desired ablation target surface, and then interpolate to a 0.1 mm pitch. Increasing the pitch from 0.4 mm to 0.1 mm increases the number of data points by 4×4=16 for each of the two gradient fields. Thus arrays involved in the Fast Fourier Transforms can be reduced in size this way. Embodiments encompass the use of data interpolation or zonal reconstruction techniques to carry out the reconstruction procedures discussed herein.

Figure 5:
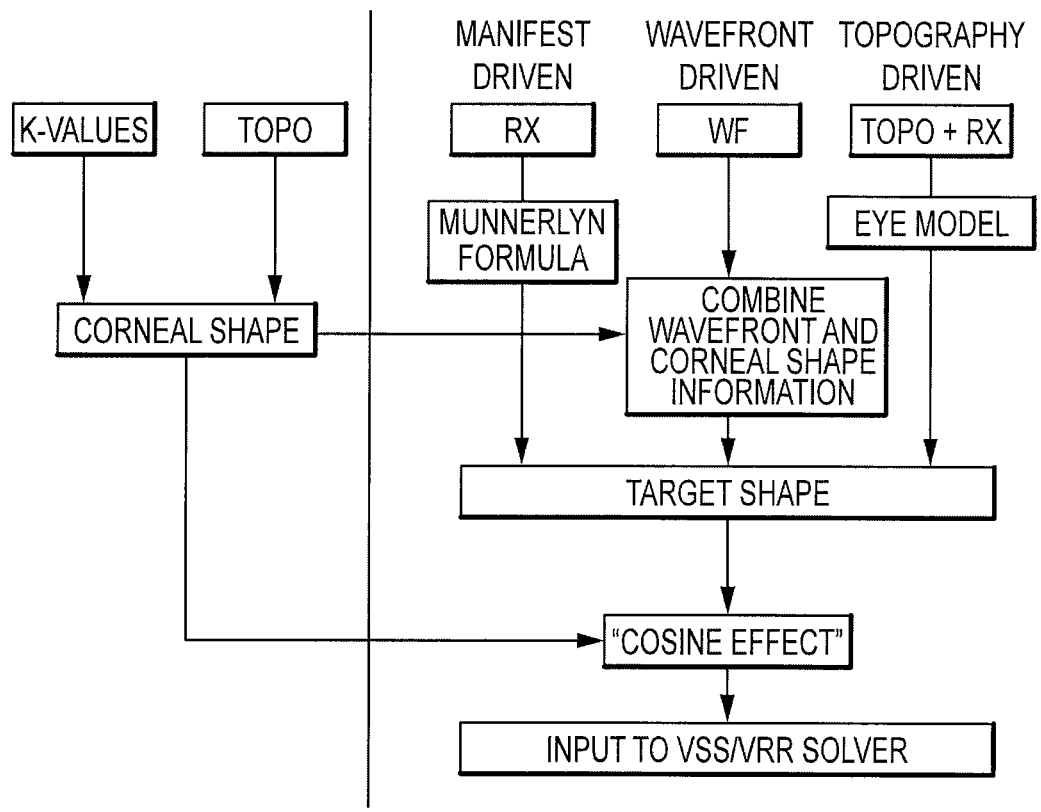
FIG. 5 provides a schematic diagram of target ablation shape methods according to embodiments of the present invention.

As described herein, system and methods embodiments of the present invention encompass techniques for combining topography and wavefront data to refine a ablation target shape. FIG. 5 provides a schematic diagram of how the present techniques can be used in practice. As shown here, embodiments may utilize K-values to estimate corneal shape. Embodiments may also involve using the actual shape as measured by a corneal topography instrument. Wavefront slope information and corneal shape information can be used together to calculate a target shape.

Various embodiments involve the use of measured wavefront refractive error or wavefront data, along with k-values and/or corneal topography, to plan or derive a laser refractive treatment. A laser vision correction ablation target can be created using wavefront or wavefront deflection information from a wavefront eye refraction, optionally without reconstructing a wavefront, along with anterior corneal surface information, for example, from a keratometer measurement or full corneal topography. In some cases, embodiments involve finding, calculating, or otherwise determining an ablation target. The ablation target may refer to the amount of corneal tissue to be removed in a treatment. For example, the ablation target, or At, can refer to the difference between a preoperative anterior corneal shape, or Spreop, and a postoperative anterior corneal shape, or Spostop. An ablation target can be characterized as follows.

$$At(x,y) = Spreop(x,y) - Spostop(x,y) \quad (23)$$

The gradient of the ablation target can be characterized as follows.

$$\frac{\partial At(x, y)}{\partial x} = \frac{\partial Spreop(x, y)}{\partial x} - \frac{\partial Spostop(x, y)}{\partial x} \quad (24)$$

$$\frac{\partial At(x, y)}{\partial y} = \frac{\partial Spreop(x, y)}{\partial y} - \frac{\partial Stpostop(x, y)}{\partial y} \quad (25)$$

In some instances, a method of determining or finding an ablation target may include measuring a surface shape of a corneal surface, and directly calculating a gradient of a preoperative anterior corneal surface from the measured surface shape of the preoperative corneal surface. Gradients of the preoperative anterior corneal shape can be determined without determining the actual preoperative shape. The method may also include finding or calculating the gradient of the desired postoperative anterior corneal surface using the measured wavefront or wavefront gradient, the desired wavefront gradient, and a known or determined preoperative anterior corneal surface gradient. Hence, it is possible to determine the postoperative corneal surface gradient values that will give the desired correction using the preoperative wavefront gradient values, the preoperative corneal gradient values, and the desired refractive result. Methods may also include reconstructing the ablation target from its gradient information. For example, methods may include reconstructing an ablation target from ablation target gradient information as determined by Eqs. (24) and (25).

Figure 6:
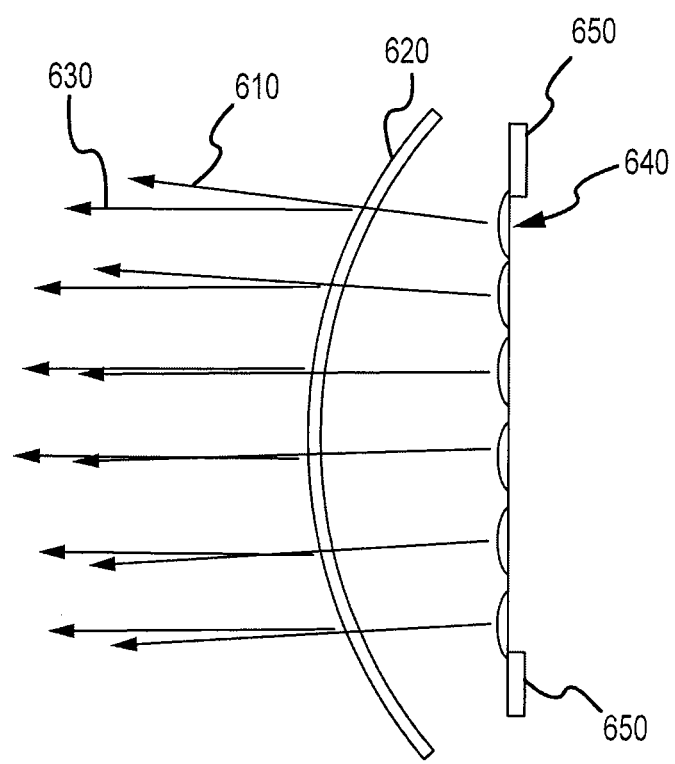
FIG. 6 illustrates aspects of an exemplary technique for determining an ablation target, according to embodiments of the present invention.

Techniques for determining an ablation target can be based on certain parameters or information. For example, as indicated in FIG. 6, in some cases the information used to calculate an ablation target can include the measured exiting wavefront gradient values 610, or ray direction information. The information used to calculate an ablation target may also include a measured anterior corneal shape 620, for example full topography or keratometer measurements with a surface reconstruction. Relatedly, the information used to calculate an ablation target may include a desired final refractive error 630. As depicted here, the rays 610 represent the central rays exiting the Hartmann-Shack lenslet images 640 located in the exit pupil of the eye which is disposed within a visible iris 650.

According to some embodiments, before and after a laser vision correction or treatment, rays from a Hartmann-Shack retinal source follow the same paths until they reach the anterior corneal surface. It is possible to determine the ray directions just before final refraction based on a measurement of the exiting rays 610 and the corneal surface 620. Relatedly, it is possible to use this ray direction information, which is just prior to final refraction, to calculate desired change in the anterior corneal surface shape, so that the rays, following final refraction, take the desired paths as represented by desired final refractive error 630.

Figure 7:
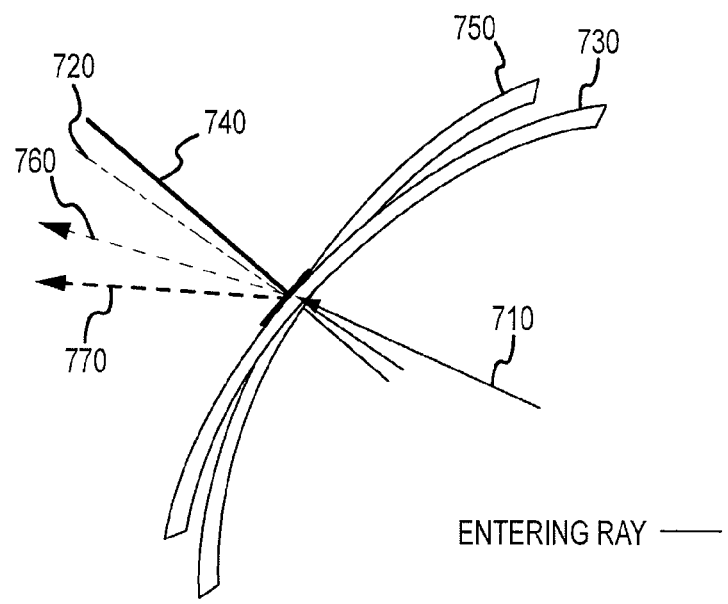
FIG. 7 illustrates aspects of an exemplary technique for determining an ablation target, according to embodiments of the present invention.

FIG. 7 illustrates aspects of exemplary techniques that involve finding or determining a desired anterior corneal gradient. As shown here, the technique can be based on or involve features such as an entering ray 710, an uncorrected surface normal 720 corresponding to an uncorrected surface 750, a corrected surface normal 740 corresponding to a corrected surface 730, an uncorrected exiting ray 760 corresponding to an uncorrected surface 750, and a corrected exiting ray 770 corresponding to a corrected surface 730.

According to some embodiments, methods or systems may involve inputting an uncorrected surface normal 720, determining a corrected surface normal 740 based on the uncorrected surface normal 720, an uncorrected exiting ray 760, and a corrected exiting ray 770, and determining an ablation target based on the uncorrected surface normal 720 and the corrected surface normal 740.

According to some embodiments, wavefront data can be used to determine ray 760 of the uncorrected cornea and the topography data can be used to determine surface normal 720 of the uncorrected cornea. Using 720 and 760, the ray 710 into the cornea (from the retina) can be calculated. Finally, based on the desired output ray 770 (the corrected performance), the direction of the surface normal 740 of the corrected cornea can be calculated. Having the uncorrected and corrected surface normals the ablation target may be calculated for the laser. Hence, methods of determining an ablation target can include selecting an ocular performance of an eye, measuring or calculating a first parameter having at least one of a wavefront from an eye or a slope of a wavefront from the eye, and measuring or calculating a second parameter having at least one of a shape a cornea of the eye or a slope of the corneal shape of the eye. Such methods may be based on the use of Eqs. 10N and 10O, for example. Methods may also include determining an input parameter having a direction of propagation out of the eye, where the calculation of the input parameter is based on the first parameter and the second parameter. Methods may also include determining an ablation target based on the selected ocular performance and the input parameter. According to some embodiments, the eye has an optical axis and the ocular performance is an angle of a ray from an object at a specified location from the eye along the optical axis. The object can be a point source disposed on the optical axis an infinite distance from the eye. The first parameter can be determined using a wavefront sensor and the second parameter can be determined from a topography measurement. In some case, the wavefront sensor is a Hartmann-Shack wavefront sensor. In some cases, the input parameter is a ray propagating from a retina of the eye. Optionally, the first parameter, the second parameter, and the input parameter can be specified from a predetermined location on the cornea. Embodiments of the present invention also encompass systems for performing such methods, where the systems may include memory for storing the inputs and/or measurements, and a processor for making the calculations described.

According to some embodiments, methods involve projecting measured wavefront gradient values onto a specified corneal ablation grid. Methods may also involve calculating ablation target gradient values from pre-operative corneal surface gradients, wavefront gradient values, and desired wavefront gradient values using ray tracing formulas. Further, methods may include reconstructing an ablation target from its gradient values.

Figure 8:
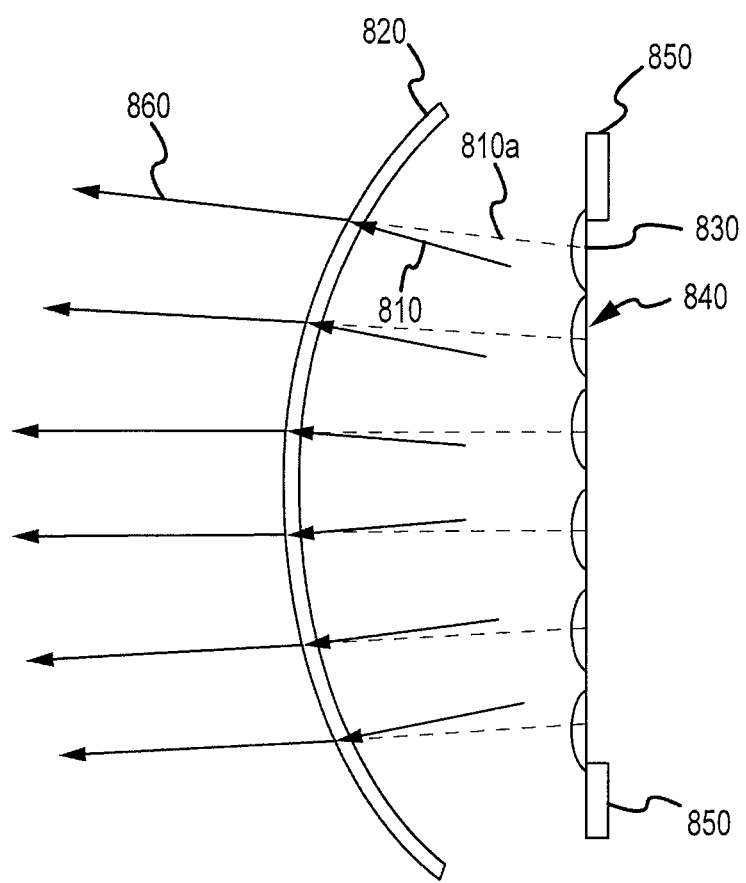
FIG. 8 illustrates aspects of an exemplary technique for determining an ablation target, according to embodiments of the present invention.

FIG. 8 illustrates aspects of an exemplary techniques that involve finding or determining a desired anterior corneal gradient. In some cases, a technique may involve the projection of measured rays 810*a* onto a corneal surface 820. Rays 810 can refer to rays just prior to refraction at the anterior corneal surface, or entering rays. As shown here, rays can be measured at a measurement location 830, which corresponds to a Hartmann-Shack lenslet image plane in the exit pupil of the eye 840 which is disposed within a visible iris 850. Rays 860 represent rays exiting the uncorrected or preoperative eye.

Figure 9:
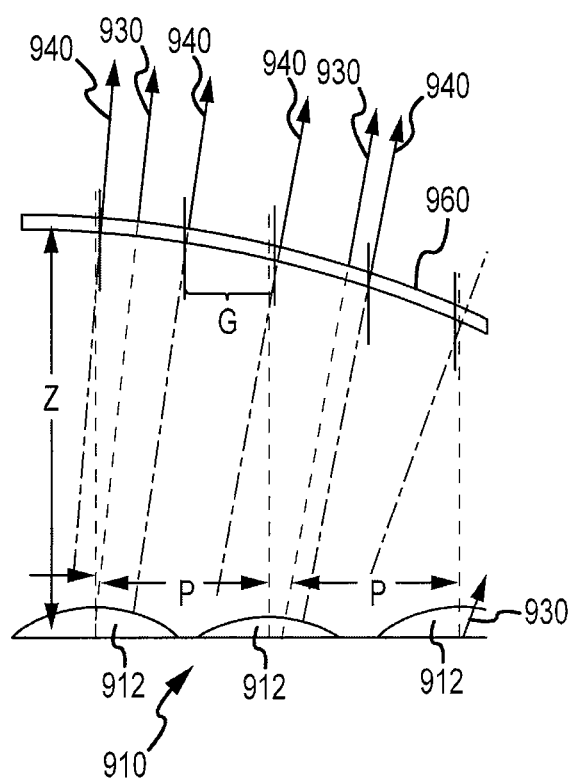
FIG. 9 illustrates aspects of an exemplary technique for determining an ablation target, according to embodiments of the present invention.

As shown in FIG. 9, Hartman-Shack lenslet array 910 has a pitch P, and includes lenslets 912 at a lenslet array plane 920. Lenslets 912 are spaced apart by pitch P in the lenslet plane array. Rays 930 are measured by the Hartmann-Shack array 910. Methods may involve selecting ablation grid locations. For example, it is possible to select an ablation grid patch with a chosen ablation grid spacing G. Rays 940 that would strike the corneal surface 960 are spaced apart by the chosen ablation grid pitch G on the corneal surface 960. Measured rays 930 can be interpolated to find rays 940 that strike the corneal surface 960 at chosen ablation grid locations. The Z shown in FIG. 9 can be equivalent to the z discussed in reference to Eq. 13B, which represents the distance from the corneal vertex plane to the corneal surface at the intersection point for a ray.

Exemplary techniques can involve the use of ray-tracing formulas to find the new surface gradient values. Snell's law in vector form can be represented as follows.

$$|R_{entering}\rangle = \frac{|R_{wavefront}\rangle - \Gamma|N_{cornea}\rangle}{n_{stroma}} \qquad (26)$$

$$\Gamma = n_{air}\rangle R_{wavefront}|N_{cornea} \qquad (27)$$
$$\left\langle -\sqrt{n_{air}^2\langle\rangle R_{wavefront}|N_{cornea}\langle^2-1\rangle + n_{stroma}^2}\Gamma = n_{air}\right\rangle$$
$$R_{wavefront}|N_{cornea}\langle -\sqrt{n_{air}^2\langle\rangle R_{wavefront}|N_{cornea}\langle^2-1\rangle + n_{stroma}^2}$$

Because the entering rays are the same before and after ablation, it is possible to calculate as follows.

$$\Gamma'|N'_{cornea}\langle = |R_{wavefront\ desired}\langle - |R_{wavefront}\langle + \Gamma|N_{cornea}\langle \qquad (28)$$

Dividing the component equations gives the x- and y-gradient values.

$$\frac{Rx_{wavefront\ desired} - Rx_{wavefront} + \Gamma Nx_{cornea}}{Rz_{wavefront\ desired} - Rz_{wavefront} + \Gamma Nz_{cornea}} = \frac{\Gamma' Nx'_{cornea}}{\Gamma' Nz'_{cornea}} \qquad (29)$$
$$= \frac{Nx'_{cornea}}{Nz'_{cornea}}$$
$$= \frac{\partial Spostop(x, y)}{\partial x}$$

$$\frac{Ry_{wavefront\ desired} - Ry_{wavefront} + \Gamma Ny_{cornea}}{Rz_{wavefront\ desired} - Rz_{wavefront} + \Gamma Nz_{cornea}} = \frac{\Gamma' Ny'_{cornea}}{\Gamma' Nz'_{cornea}} \qquad (30)$$
$$= \frac{Ny'_{cornea}}{Nz'_{cornea}}$$
$$= \frac{\partial Spostop(x, y)}{\partial y}$$

An ablation target can be reconstructed from the difference in the corneal surface gradients before and after ablation, as follows.

$$\frac{\partial At(x, y)}{\partial x} = \frac{\partial Spreop(x, y)}{\partial x} - \frac{\partial Spostop(x, y)}{\partial x} \qquad (31)$$

$$\frac{\partial At(x, y)}{\partial y} = \frac{\partial Spreop(x, y)}{\partial y} - \frac{\partial Spostop(x, y)}{\partial y} \qquad (32)$$

According to some embodiments, Fourier gradient reconstruction allows rapid, accurate reconstruction due to the fact that the gradient data have been prepared on a square grid.

Embodiments disclosed herein provide certain technical advantages. For example, embodiments encompass techniques that involve the full integration of wavefront and corneal surface information. Full corneal topography can provide more accurate corneal height information for a ray interpolation step, more accurate local corneal gradient information for a reconstruction step, and more accurate laser ablation compensation to be made for tipped surface effects. Moreover, full use can be made of wavefront information without the need to reconstruct the wavefront. In some cases, there is no need to decide on the wavefront reconstruction method used.

Each of the above calculations or operations may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

While the exemplary embodiments have been described in some detail, by way of example and for clarity of understanding, those of skill in the art will recognize that a variety of modification, adaptations, and changes may be employed. Hence, the scope of the present invention should be limited solely by the claims.

APPENDIX A

A Simplified Method to Find the Taylor Expansion of Zernike Polynomial Functions Any function, that has a value at location (x,y) of f(x,y) and that has partial derivatives of all orders may be evaluated at location (x+dx,y+dy) using the Taylor expansion $$f(x+dx, y+dy) = \sum_{k=0}^{\infty} \frac{(-1)^k}{k!} \left( dx \frac{\partial}{\partial x} + dy \frac{\partial}{\partial y} \right)^k f(x, y) \quad \text{(A1)}$$

Any function, f(x,y), may also be expanded using a complete set of orthogonal functions, $A_i(x,y)$, with suitable weighting coefficients, $a_i$, and represented as $$f(x, y) = \sum_{i=0}^{\infty} a_i A_i(x, y)) \quad \text{(A2)}$$

By inserting Eq. (A2) into Eq. (A1) it can be shown that $$f(x+dx, y+dy) = \sum_{k=0}^{\infty} \frac{(-1)^k}{k!} \left( dx \frac{\partial}{\partial x} + dy \frac{\partial}{\partial y} \right)^k \sum_{i=1}^{\infty} a_i A_i(x, y) \quad \text{(A2a)}$$

Because $a_i$ is not a function of x or y it is not effected by the action of the partial differential operators and so the expression may be rearranged to read $$f(x+dx, y+dy) = \sum_{i=1}^{\infty} a_i \sum_{k=0}^{\infty} \frac{(-1)^k}{k!} \left( dx \frac{\partial}{\partial x} + dy \frac{\partial}{\partial y} \right)^k A_i(x, y) \quad \text{(A3)}$$

In some embodiments, use of Eq. (A3) generally involves the calculation and evaluation of partial derivatives of all orders for all members of the orthogonal set. However for a special class of orthogonal functions whose first partial derivatives may be expressed as sums of the original set itself, the evaluation of Eq. (A3) may be greatly simplified as described below. The Zernike polynomial functions represent one such set of this special class of orthogonal functions. Aspects of this observation are discussed in R. J. Noll, "Zernike polynomials and atmospheric turbulence", J. Opt. Soc. Am. 66, 207-11 (1976). This special class of orthogonal can be represented by the symbol Z.

The first partial derivatives of a member of a special orthogonal set can be given by the following sums $$\frac{\partial Z_i(x, y)}{\partial x} = \sum_{j=1}^{\infty} Dx_{ij} Z_j(x, y) \quad \text{(A4)}$$

$$\frac{\partial Z_i(x, y)}{\partial y} = \sum_{j=1}^{\infty} Dy_{ij} Z_j(x, y) \quad \text{(A5)}$$

where the $Dx_{ij}$ and $Dy_{ij}$ are weighting coefficients. By representing the first partial derivatives of all members of the special orthogonal function set by the column vectors $$|\partial Zx\rangle = \begin{vmatrix} \frac{\partial}{\partial x} Z_1 \\ \frac{\partial}{\partial x} Z_2 \\ \vdots \\ \frac{\partial}{\partial x} Z_j \\ \vdots \end{vmatrix} \text{ and } |\partial Zy\rangle = \begin{vmatrix} \frac{\partial}{\partial y} Z_1 \\ \frac{\partial}{\partial y} Z_2 \\ \vdots \\ \frac{\partial}{\partial y} Z_j \\ \vdots \end{vmatrix} \quad \text{(A5a)}$$

the members of the orthogonal function set itself by the column vector $$|Z\rangle = \begin{vmatrix} Z_1 \\ Z_2 \\ \vdots \\ Z_j \\ \vdots \end{vmatrix} \quad \text{(A5b)}$$

and the weighting coefficients by two matrices $$|Dx| = \begin{vmatrix} Dx_{11} & Dx_{12} & \cdots & Dx_{1j} & \cdots \\ Dx_{21} & Dx_{22} & \cdots & Dx_{2j} & \cdots \\ \vdots & \vdots & \ddots & & \\ Dx_{j1} & Dx_{j2} & & Dx_{jj} & \\ \vdots & \vdots & & & \ddots \end{vmatrix} \quad \text{(A5c)}$$

and $$|Dy| = \begin{vmatrix} Dy_{11} & Dy_{12} & \cdots & Dy_{1j} & \cdots \\ Dy_{21} & Dy_{22} & \cdots & Dy_{2j} & \cdots \\ \vdots & \vdots & \ddots & & \\ Dy_{j1} & Dy_{j2} & & Dy_{jj} & \\ \vdots & \vdots & & & \ddots \end{vmatrix}$$

the ensemble of equations given by (A4) and (A5) may be represented by the compact matrix equations $$|\partial Zx\rangle = |Dx||Z\rangle \quad (A6)$$

$$|\partial Zy\rangle = |Dy||Z\rangle \quad (A6a)$$

Now consider the second partial derivatives of the special orthogonal functions. For instance, using the formalism of equations (A6 and A6a), it is possible to write the second partial derivatives with respect to x as $$\frac{\partial}{\partial x}\Big|\partial Zx\Big\rangle = \frac{\partial}{\partial x}|Dx|\Big|Z\Big\rangle \quad (A6b)$$

Because none of the elements of the coefficient matrix |Dx| are functions of x, this expression can be written as $$\frac{\partial}{\partial x}\Big|\partial Zx\Big\rangle = |Dx|\Big(\frac{\partial}{\partial x}\Big|Z\Big\rangle\Big) = |Dx||\partial Zx\rangle = |Dx||Dx||Z\rangle \quad (A6c)$$

Notation can be defined as $$\frac{\partial}{\partial x}\Big|\partial Zx\Big\rangle \equiv |\partial Zxx\rangle;\ \frac{\partial}{\partial y}\Big|\partial Zx\Big\rangle \equiv |\partial Zxy\rangle;\ \frac{\partial}{\partial y}\Big|\partial Zy\Big\rangle \equiv |\partial Zyy\rangle \quad (A6d)$$

The expressions for the three second partial derivatives of the special orthogonal functions can be written $$|\partial Zxx\rangle = |Dx||Dx||Z\rangle = |Dx|^2|Z\rangle$$

$$|\partial Zxy\rangle = |Dx||Dy||Z\rangle$$

$$|\partial Zyy\rangle = |Dy||Dy||Z\rangle = |Dy|^2|Z\rangle \quad (A7)$$

In some embodiments, the order of application of the transformation matrices in the mixed partial set may be immaterial because for an analytic function $$\frac{\partial}{\partial x}\Big(\frac{\partial F}{\partial y}\Big) = \frac{\partial}{\partial y}\Big(\frac{\partial F}{\partial x}\Big).$$

This can also be true of higher order mixed partial derivatives.

In equations (A7), second partial derivatives can be determined without prior determination of any of partial derivatives of the members of the special orthogonal set. In some embodiments, new coefficient matrices are not created. Having once found the elements of the first partial derivative matrices, matrix multiplication is the only additional step needed to calculate the second partial derivatives.

This formalism may be repeated for the higher order partial derivatives and a general expression for the nth order partial derivatives of a set of special orthogonal functions may be given as $$|\partial Zx_1 \ldots x_m y_1 \ldots y_n\rangle = |Dx|^m |Dy|^n |Z\rangle \quad (A8)$$

Based on these elements, it is possible to simplify Eq. (3), which can be written for the case of this special class of orthogonal functions with symbol Z replacing symbol A.

$$f(x+dx, y+dy) = \sum_{i=1}^{\infty} a_i \sum_{k=0}^{\infty} \frac{(-1)^k}{k!}\Big(dx\frac{\partial}{\partial x} + dy\frac{\partial}{\partial y}\Big)^k Z_i(x,y) \quad (A8a)$$

The inner sum normally involves a calculation of each partial derivative of the orthogonal set but as has just been shown, this may not be the case for a special orthogonal set. Therefore by identifying the partial derivative operators $$\frac{\partial}{\partial x} \text{ and } \frac{\partial}{\partial y}$$

with the matrix operators |Dx| and |Dy| respectively, equation (A3) can be written as $$f(x+dx, y+dy) = \Big\langle a\Big|\sum_{k}^{\infty}\frac{(-1)^k}{k!}(dx|Dx|+dy|Dy|)^k\Big|Z(x,y)\Big\rangle \quad (A9)$$

Eq. (A2) has the form of an inner product so that by defining a row vector of coefficients $a_i$ as $$\langle a| = [a_1\ a_2\ \ldots\ a_i\ \ldots] \quad (A9a)$$

(A2) becomes $$f(x,y) = \sum_{i=0}^{\infty} a_i Z_i(x,y)) = \langle a|Z(x,y)\rangle \quad (A9b)$$

leading to the above formalism in (A9).

The quantity $$\Big|\sum_{k}^{\infty}\frac{(-1)^k}{k!}(dx|Dx|+dy|Dy|)^k\Big|$$

is a matrix as it consists of products of matrices and the constants k, dx and dy. It is not a function of position variables x and y so it may be evaluated separately in the sense of making it into a single matrix. This single matrix can be referred to as the translation matrix |T|. This allows (A9) to be written as $$f(x+dx, y+dy) = \langle a|T|Z(x,y)\rangle \quad (A10)$$

where $$T = \Big|\sum_{k}^{\infty}\frac{(-1)^k}{k!}(dx|Dx|+dy|Dy|)^k\Big| \quad (A11)$$

Because the special orthogonal sets are complete sets they can have a infinite number of members. In some embodiments, due to practical considerations, only a limited subset may be used. In the case of some embodiments involving Zernike polynomials, the highest exponential power of any polynomial is the radial order of the polynomial. In such embodiments all derivatives of power higher than the order are zero identically and the value of k in the T sum need never be higher than the highest order in the set chosen.

The matrix operators |Dx| and Dy| for Zernike polynomial functions can be quite simple. In some embodiments they are sparse lower triangle matrices with zeros in all elements of their diagonals. By sparse, it can be meant the many of the elements in the lower triangular portion of the matrices are zero. Rules for finding their non zero values are given in the paper by Noll, discussed infra, for the case of normalized Zernike functions. In some embodiments, normalized Zernike functions are the products of a radial polynomial, a sinusoidal azimuthal function and a normalization constant. This can make many of the non-zero elements in the matrices have square roots in them. In some embodiments, if un-normalized Zernike functions (which lack the normalization constant in the product) are used, all non-zero elements in the matrices are simple integers and so it can be easier to construct matrices for the un-normalized Zernike functions. Because Zernike functions are products, when taking the inner product of the Zernike functions and their respective coefficients to find f(x,y), the normalization factors can either be included in the Zernike functions (the normalized case) or in the coefficients (the un-normalized case). Therefore if coefficients in normalized form are provided and it is desirable to use the simple forms of |Dx| and Dy| the normalized coefficients can be converted to un-normalized coefficients by multiplying each by the correct normalization factor before use in Eq. (A9). When the Zernike functions are labeled using standard double index notation, $Z_n^m$, the normalization factor is given by $$N_n^m = \sqrt{(2-\delta_{m0})(n+1)} \quad (A12)$$

where $\delta_{m0}$ is the Kronecker delta which equals zero unless m=0.

In some embodiments, rules for assigning values to the elements can be complex and it may be desirable to use a computer routine to generate them. An appropriate algorithm is given as a computer routine in Appendix B.

In some embodiments, the first partial derivative matrix operators |Dx| and |Dy| for Zernike functions can be useful when determining the local curvature at any location on a surface that may be represented by a set of Zernike coefficients in that the first and second derivatives used for the calculation can be easily determined with their use.

APPENDIX B

A computer algorithm to generate partial derivative values for a surface specified by a standard set of Zernike coefficients at locations specified by meshgrids X and Y is provided below.

```
function [dZx,dZy]=stdzernikegradient(X,Y,sc,mask);
%STDZERNIKEGRADIENT
%       STDZERNIKEGRADIENT returns two vector fields of x and y
%       gradient values for the surface specified by the
%       set of standard Zernike coefficients, "sc", (as per ANSI
%       Z80.28-2004) whose first element is the aperture diameter, on
%       the x and y locations specified by meshgrids X and Y within
%       the apeture diameter. The diameter is given in millimeters.
%       The coefficients are given in microns.
%
%       A logical mask the size of X and Y may be specified. Otherwise a
%       circular mask is internally generated the size of the diameter
%       specified by the Zernike coefficient set.
%
%       Special functions called by STDZERNIKEGRADIENT
%       UNNORMALIZEDZERNIKE - calculates an un-normalized
%                             Zernike function with indices m and n at
%                             positions r and theta
%       ZPARTIALS - generates Zernike partial derivative generation
%                   matrices
%
%       [dZx,dZy]=stdzernikegradient(X,Y,sc);
%
%
terms=length(sc)-1; %       number of terms to be evaluated
cn=[sc(1)/2;sc(2:end)*1e-3]; %      convert from microns to millimeters
aperture=sc(1)/2;
%       convert to un-normalized coefficients
for j=1:terms
    n=ceil((sqrt(1+j*8)-3)/2);
    m=2*j-n*(n+2)-2;
  if m==0
        coef(j)=cn(j+1)*sqrt(n+1);
else
        coef(j)=cn(j+1)*sqrt(2*n+2);
    end
end
coef=coef';
% routine to insure that only the surface within the aperture is used to
find coefficients
if nargin<4   %      create a mask if none is input
    mask=ones(size(X)).*(sqrt(X.^2+Y.^2)<=aperture);
[th,rr]=cart2pol(X,Y); % convert from Cartesian to polar coordinates
r=rr(:);           %       covert from an array to a column vector
theta=th(:);       %       covert from an array to a column vector
%       rescale/normalize data to aperture size
r=r/aperture;  %       vector of scaled r values
order=ceil((sqrt(1+terms*8)-3)/2); %    calculate the maximum radial
%       index n, the order
% Form Zernike term vectors, these are stored in matrix Z
Z=zeros(size(r,1),fix(.5*(order+1)*(order+2))); % initial matrix Z
for j=1:terms
    n=ceil((sqrt(1+j*8)-3)/2);
    m=2*j-n*(n+2)-2;
    Z(:,j)=unnormalizedzernike(n,m,r,theta);
end
[Dx,Dy]=zpartials(order);   %      form partial derivative matrices
Zdx=Z*Dx';    %      form partial derivatives of Z with respect to x
Zdy=Z*Dy';    %      form partial derivatives of Z with respect to y
dzzx=Zdx(:,1:terms)*coef/aperture; %   first x partial derivative
dzzy=Zdy(:,1:terms)*coef/aperture; %   first y partial derivative
[m,n]=size(X);
dzx = reshape(dzzx,[m n]);
dzy = reshape(dzzy,[m n]);
dZx= dzx.*mask;       % only the values inside the aperture are allowed
to be non zero
dZy= dzy.*mask;       % only the values inside the aperture are allowed
to be non zero
%============================================
```

Computer Algorithm to Generate Partial Derivative Weighting Matrices for Un-Normalized Zernike Polynomial Functions The following is an example of a routine, written in MatLab code, to generate the partial derivative weighting matrices. However the code is easily converted to C++ code since it consists of simple 'for' loops.

```
function [Dx,Dy]=zpartials(order)
%ZPARTIALS
%[Dx,Dy]=zpartials(order);
%       This function creates x and y partial derivative weighting
%       matrices, Dx and Dy, which allow the partial derivatives
%       of un-normalized Zernike polynomial functions to be formed,
%       through the specified radial order (order),
```

-continued

```
%    as sums of the Zernike functions themselves.
terms=fix(.5*order*(order+3))+1;        % number of terms
Dx=zeros(terms);   %    initialize the x partial derivative matrix to zero
Dy=zeros(terms);   %    initialize the y partial derivative matrix to zero
% The partial derivative matrices are square matrices of size (terms ×
terms)
r=0;    % initialize the row index
c=0;    % intialize the column index
for i=1:order+1     % i= n+1 where n is the radial index of the function
   % whose partial is to be formed
   for j=1:i % index associated with the azimuthal index m
      r=r+1; %
      m=2*j-i-1;
      if m==0
         delta=1;
      else
         delta=0;
      end
      mm=abs(m)-1;
      mp=abs(m)+1;
      s=sign(m);
      if s==0
         s=1;
      end
      if mm>0
         for np=mm:2:i-2
            cx=fix(.5*(np*(np+2)+s*mm))+1;
            cy=fix(.5*(np*(np+2)-s*mm))+1;
            Dx(r,cx)=(1+delta)*(np+1);
            Dy(r,cy)=-s*(1+delta)*(np+1);
         end
      end
      if mm==0&s>0
         for np=mm:2:i-2
            cx=fix(.5*np*(np+2))+1;
            Dx(r,cx)=(1+delta)*(np+1);
         end
      end
      if mm==0&s<0
         for np=mm:2:i-2
            cy=fix(.5*np*(np+2))+1;
            Dy(r,cy)=-s*(1+delta)*(np+1);
         end
      end
      for np=mp:2:i-2
         cx=fix(.5*(np*(np+2)+s*mp))+1;
         cy=fix(.5*(np*(np+2)-s*mp))+1;
         Dx(r,cx)=(1+delta)*(np+1);
         Dy(r,cy)=s*(1+delta)*(np+1);
      end
   end
end
%=========================================================
```

What is claimed is:

1. A system for determining an ablation target shape for a laser vision treatment for an eye of a patient, comprising:
   a wavefront input module comprising a tangible medium embodying machine-readable code that receives a wavefront information comprising a wavefront value or a wavefront gradient value of an eye as determined by a wavefront sensor and that receives a desired wavefront value or a desired wavefront gradient value of the eye;
   a topography input module comprising a tangible medium embodying machine-readable code that receives an anterior corneal shape information comprising an anterior corneal shape value or an anterior corneal shape gradient value of the eye as determined by a corneal topography device; and
   a processing module comprising a tangible medium embodying machine-readable code that combines the wavefront value, the desired wavefront value, and the anterior corneal shape value, or the wavefront gradient value, the desired wavefront gradient value, and the anterior corneal shape gradient value, to provide the ablation target shape.

2. The system according to claim 1, wherein the system combines the wavefront value, the desired wavefront value, and the anterior corneal shape value to provide the ablation target shape.

3. The system according to claim 1, wherein the system combines the wavefront gradient value, the desired wavefront gradient value, and the anterior corneal shape gradient value to provide the ablation target shape.

4. The system according to claim 1, wherein the wavefront information comprises a wavefront gradient value.

5. The system according to claim 1, wherein the anterior corneal shape information comprises an anterior corneal shape gradient value.

6. The system according to claim 1, wherein the code of the wavefront input module receives the desired wavefront gradient value of the eye, and wherein the code of the processing module combines the wavefront gradient value, the desired wavefront gradient value, and the anterior corneal shape gradient value to provide the ablation target shape.

7. The system according to claim 1, wherein the code of the processing module provides the ablation target shape based on an ablation target gradient value.

8. The system according to claim 1, wherein the code of the processing module provides the ablation target shape based on an ablation target gradient value.

9. The system according to claim 1, wherein the tangible medium embodying machine-readable code of the processing module combines the wavefront information comprising the wavefront value or the wavefront gradient value, the desired wavefront value or the desired wavefront gradient value, and the anterior corneal shape information comprising the anterior corneal shape value or the anterior corneal shape gradient value to provide the ablation target shape by:
   obtaining a difference between the wavefront value and the desired wavefront value or the difference between the wavefront gradient value and the desired wavefront gradient value,
   obtaining an anterior corneal shape surface normal and a pre-ablation corneal surface gradient based on the anterior corneal shape information,
   obtaining a post-ablation corneal surface gradient based on the anterior corneal shape surface normal and the difference between the wavefront value and the desired wavefront value or the difference between the wavefront gradient value and the desired wavefront gradient value,
   obtaining an ablation target shape gradient based on the post-ablation corneal surface gradient and the pre-ablation corneal surface gradient, and
   obtaining the ablation target shape based on the ablation target shape gradient.

10. The system according to claim 9, wherein the gradient of the ablation target comprises a partial differential portion with respect to a first dimension and a partial differential portion with respect to a second dimension, and
   wherein the ablation target is reconstructed by integration of the gradient of the ablation target shape.

11. The system according to claim 9, wherein the gradient of the ablation target comprises a partial differential portion with respect to a first dimension and a partial differential portion with respect to a second dimension, and
   wherein the ablation target is reconstructed using a Fourier transform.

12. A system for determining an ablation target shape for a laser vision treatment of an eye of a patient, comprising:
   a wavefront sensor;
   a corneal topography device; and a processor coupled with the wavefront sensor and the corneal topography device, the processor comprising a tangible medium embodying machine-readable code that combines a desired wavefront value for the eye, a wavefront value of the eye of the patient from the wavefront sensor, and an anterior corneal shape value of the eye of the patient from the corneal topography device or that combines a desired wavefront gradient value for the eye, a wavefront gradient value of the eye of the patient from the wavefront sensor, and an anterior corneal shape gradient value so as to provide the ablation target shape.

13. The system according to claim 12, wherein the tangible medium embodying machine-readable code of the processor combines the wavefront information comprising the wavefront value or the wavefront gradient value, the desired wavefront value or the desired wavefront gradient value, and the anterior corneal shape information comprising the anterior corneal shape value or the anterior corneal shape gradient value to provide the ablation target shape by:
- obtaining a difference between the wavefront value and the desired wavefront value or the difference between the wavefront gradient value and the desired wavefront gradient value,
- obtaining an anterior corneal shape surface normal and a pre-ablation corneal surface gradient based on the anterior corneal shape information,
- obtaining a post-ablation corneal surface gradient based on the anterior corneal shape surface normal and the difference between the wavefront value and the desired wavefront value or the difference between the wavefront gradient value and the desired wavefront gradient value,
- obtaining an ablation target shape gradient based on the post-ablation corneal surface gradient and the pre-ablation corneal surface gradient, and
- obtaining the ablation target shape based on the ablation target shape gradient.

14. The system according to claim 13, wherein the gradient of the ablation target comprises a partial differential portion with respect to a first dimension and a partial differential portion with respect to a second dimension, and
wherein the ablation target is reconstructed by integration of the gradient of the ablation target shape.

15. The system according to claim 13, wherein the gradient of the ablation target comprises a partial differential portion with respect to a first dimension and a partial differential portion with respect to a second dimension, and
wherein the ablation target is reconstructed using a Fourier transform.

16. A system for determining an ablation target shape for a laser vision treatment for an eye of a patient, comprising:
- a wavefront input module comprising a tangible medium embodying machine-readable code that receives a wavefront information comprising a wavefront value or a wavefront gradient value of an eye as determined by a wavefront sensor;
- a topography input module comprising a tangible medium embodying machine-readable code that receives an anterior corneal shape information comprising an anterior corneal shape value or an anterior corneal shape gradient value of the eye as determined by a corneal topography device and that receives a desired anterior corneal shape value or a desired anterior corneal shape gradient value of the eye; and
- a processing module comprising a tangible medium embodying machine-readable code that combines the wavefront value, the desired anterior corneal shape value, and the anterior corneal shape value, or that combines the wavefront gradient value, the desired anterior corneal shape gradient value, and the anterior corneal shape gradient value, to provide the ablation target shape.

17. The system according to claim 16, wherein the system combines the wavefront value, the desired wavefront value, and the anterior corneal shape value to provide the ablation target shape.

18. The system according to claim 16, wherein the system combines the wavefront gradient value, the desired wavefront gradient value, and the anterior corneal shape gradient value to provide the ablation target shape.

19. The system according to claim 16, wherein the wavefront information comprises the wavefront gradient value.

20. The system according to claim 16, wherein the anterior corneal shape information comprises the anterior corneal shape gradient value.

21. The system according to claim 16, wherein the code of the wavefront input module receives the desired anterior corneal shape gradient value of the eye, and wherein the code of the processing module combines the wavefront gradient value, the desired anterior corneal shape gradient value, and the anterior corneal shape gradient value to provide the ablation target shape.

22. The system according to claim 16, wherein the tangible medium embodying machine-readable code of the processing module combines the wavefront information comprising the wavefront value or the wavefront gradient value, the desired wavefront value or the desired wavefront gradient value, and the anterior corneal shape information comprising the anterior corneal shape value or the anterior corneal shape gradient value to provide the ablation target shape by:
- obtaining a difference between the wavefront value and the desired wavefront value or the difference between the wavefront gradient value and the desired wavefront gradient value,
- obtaining an anterior corneal shape surface normal and a pre-ablation corneal surface gradient based on the anterior corneal shape information,
- obtaining a post-ablation corneal surface gradient based on the anterior corneal shape surface normal and the difference between the wavefront value and the desired wavefront value or the difference between the wavefront gradient value and the desired wavefront gradient value,
- obtaining an ablation target shape gradient based on the post-ablation corneal surface gradient and the pre-ablation corneal surface gradient, and
- obtaining the ablation target shape based on the ablation target shape gradient.

23. The system according to claim 22, wherein the gradient of the ablation target comprises a partial differential portion with respect to a first dimension and a partial differential portion with respect to a second dimension, and
wherein the ablation target is reconstructed by integration of the gradient of the ablation target shape.

24. The system according to claim 22, wherein the gradient of the ablation target comprises a partial differential portion with respect to a first dimension and a partial differential portion with respect to a second dimension, and
wherein the ablation target is reconstructed using a Fourier transform.

* * * * *